US006923809B2

(12) United States Patent
Eggers et al.

(10) Patent No.: US 6,923,809 B2
(45) Date of Patent: Aug. 2, 2005

(54) MINIMALLY INVASIVE INSTRUMENTATION FOR RECOVERING TISSUE

(75) Inventors: Philip E. Eggers, Dublin, OH (US); Andrew R. Eggers, Ostrander, OH (US); Eric A. Eggers, Columbus, OH (US); David Jacobs, Acton, MA (US)

(73) Assignee: Neothermia Corporation, Natick, MA (US)

( * ) Notice: Subject to any disclaimer, the term of this patent is extended or adjusted under 35 U.S.C. 154(b) by 110 days.

(21) Appl. No.: 10/630,488

(22) Filed: Jul. 30, 2003

(65) Prior Publication Data

US 2005/0033286 A1 Feb. 10, 2005

(51) Int. Cl.[7] ............................................. A61B 18/14
(52) U.S. Cl. ........................................................ 606/45
(58) Field of Search .............................. 606/41, 45, 49

(56) References Cited

U.S. PATENT DOCUMENTS

| | | |
|---|---|---|
| 6,277,083 B1 | 8/2001 | Eggers et al. |
| 6,287,304 B1 * | 9/2001 | Eggers et al. .................. 606/45 |
| 6,471,659 B2 | 10/2002 | Eggers et al. |

OTHER PUBLICATIONS

Parker, Steve H. "The Advanced Breast Biopsy Instrumentation: Another Trojan Horse?" *Am. J. Radiology* 171: 61–53 (1998).

D'Angelo, Philip C., et al. "Stereotactic Excisional Breast Biopsies Utilizing the Advanced Breast Biopsy Instrumentation System" *Am J Surg.* 174: 297–302 (1997).

Ferzli, George S., et al. "Advanced Breast Biopsy Instrumentation: A Critique", *J Am Coll Surg.* 185: 145–151 (1997).

Rosen, Paul Peter, *Rosen's Breast Pathology*, Philadelphia: Lippincott–Raven Publishers, pp. 837–858 (1997).

Parker, Steve H., Needle,) *Percutaneous Breast Biopsy* Eds. Parker, et al, Raven Press, new York, pp 7–14 (1993).

Parker, Steve H. "Stereotactic Large–Core Breast Biopsy," *Percutaneous Breast Biopsy* Eds. Parker, et al, Raven Press, new York, pp. 61–79 (1993).

* cited by examiner

*Primary Examiner*—Lee S. Cohen
(74) *Attorney, Agent, or Firm*—Mueller and Smith, LPA

(57) ABSTRACT

The capture component of tissue retrieval apparatus is strengthened to improve its structural integrity when utilized within very dense tissue. Eyelet structures carrying pursing cable are improved through the utilization of slightly expanded constant widths with diminished lengths to avoid fold back phenomena. The pursing cables employed with the capture component exhibit more than a 100% improvement in tensile strength at high electrosurgical cutting temperatures through the utilization of strands having about a 1.4 mil diameter formed with a type 316 stainless steel.

45 Claims, 15 Drawing Sheets

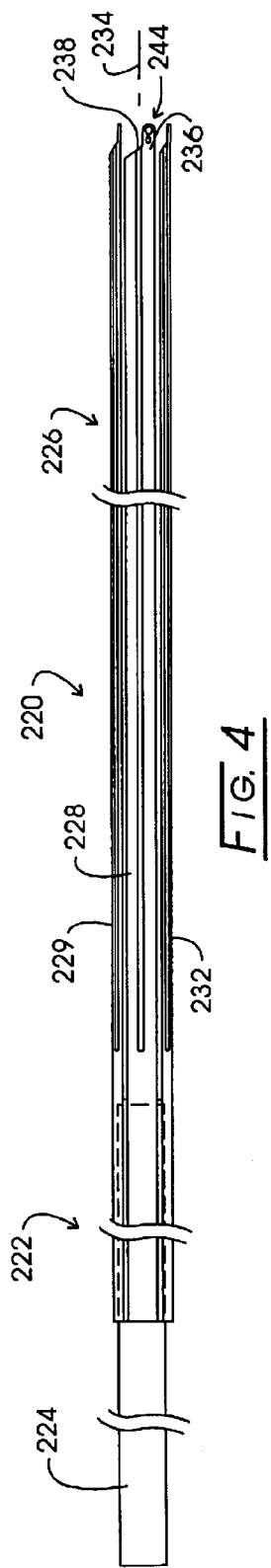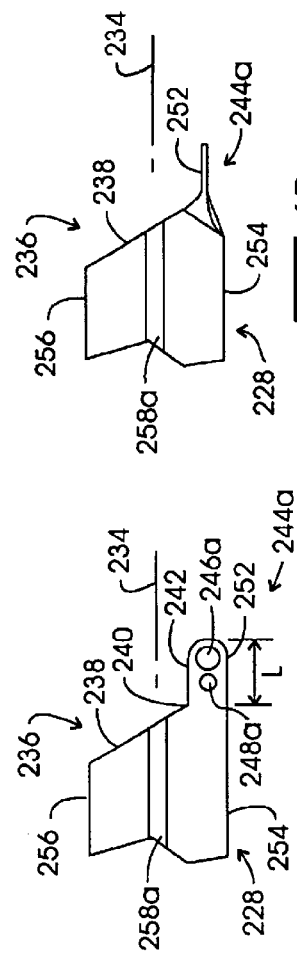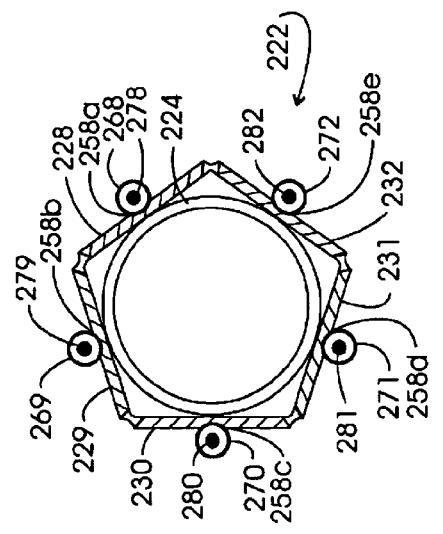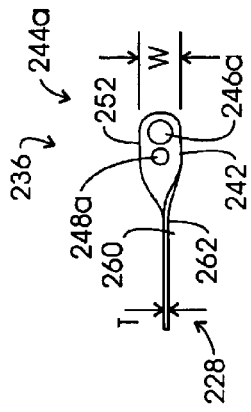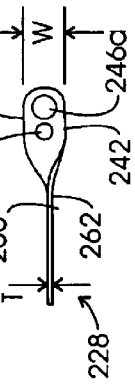

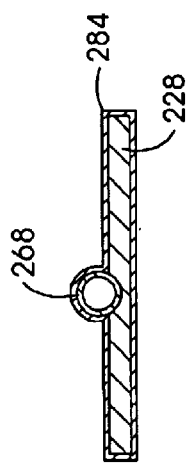
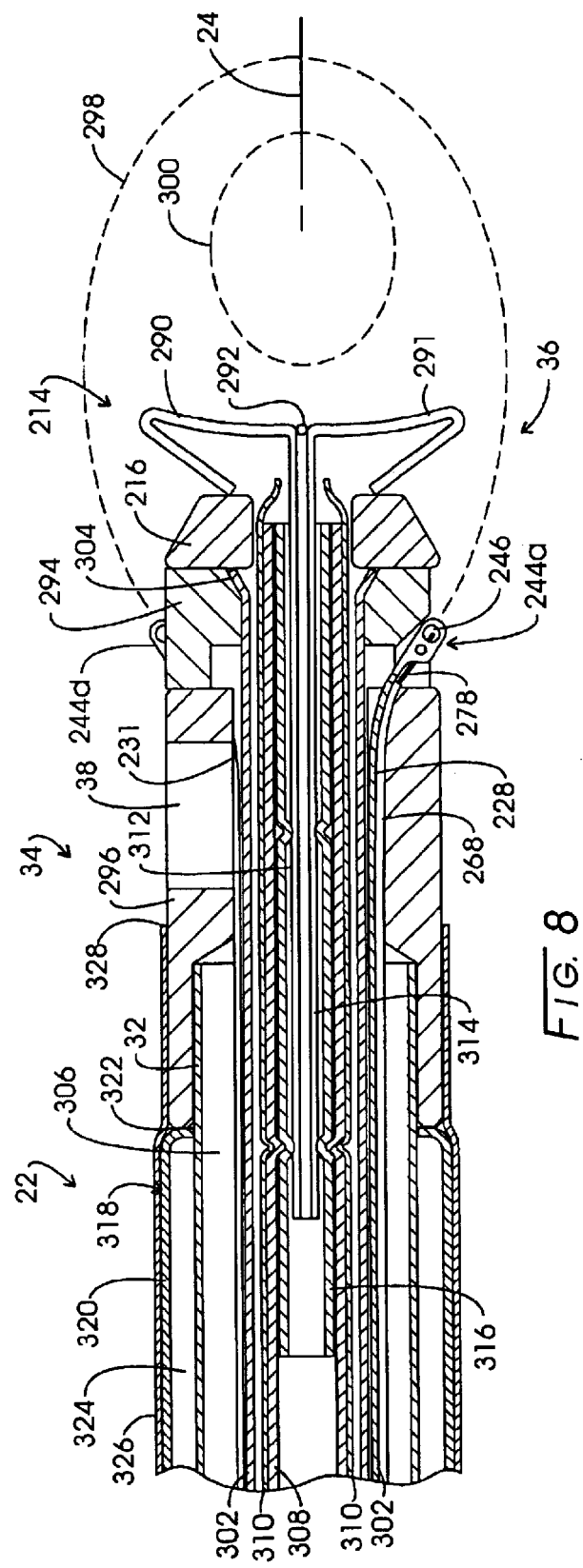
FIG. 7
FIG. 8

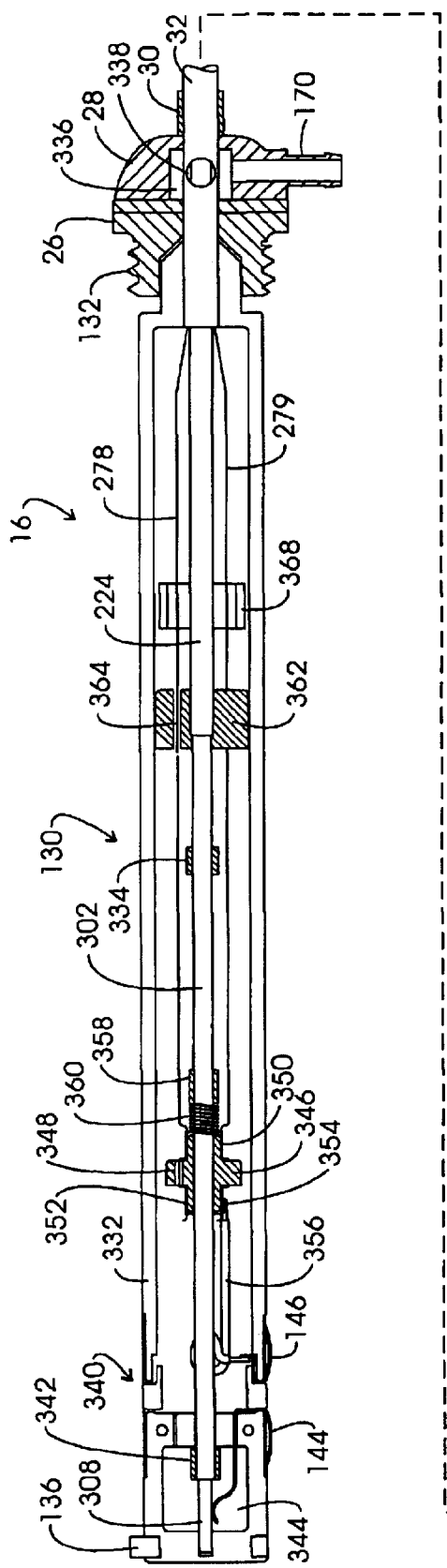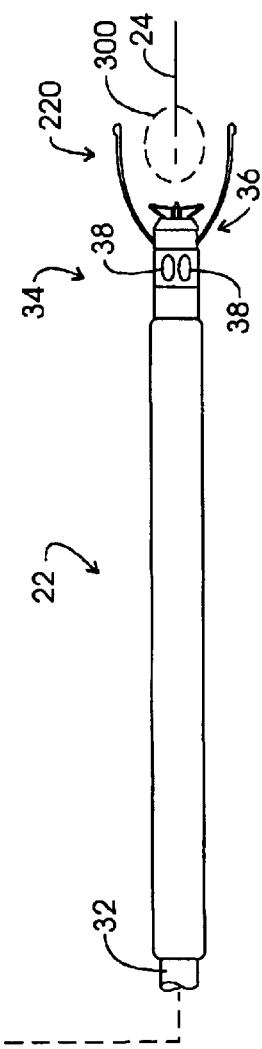
FIG. 12

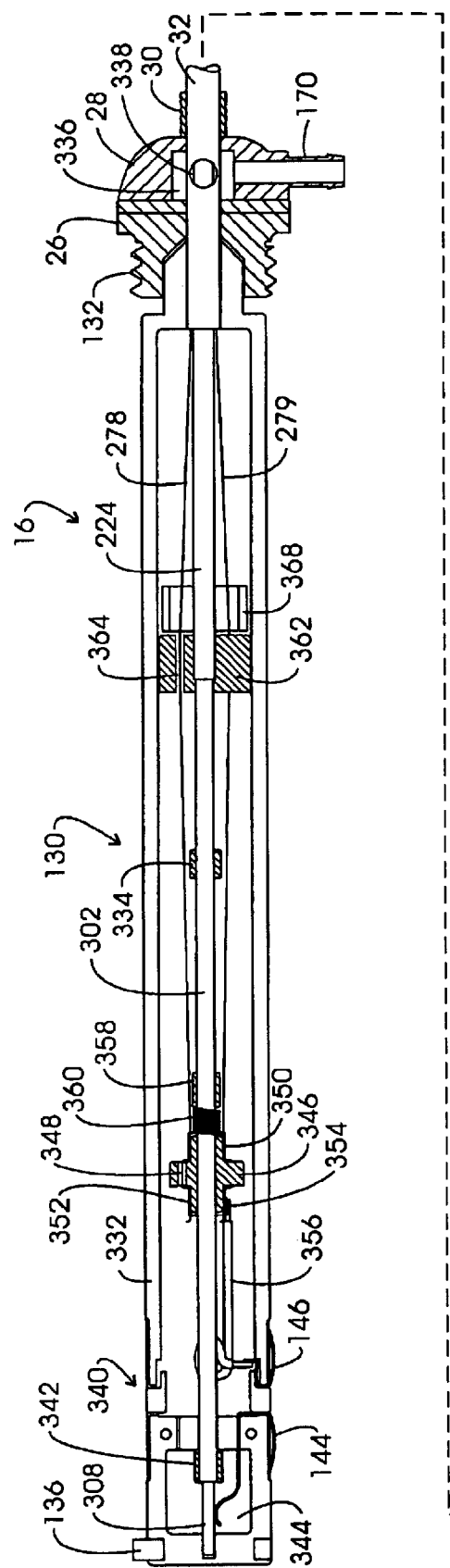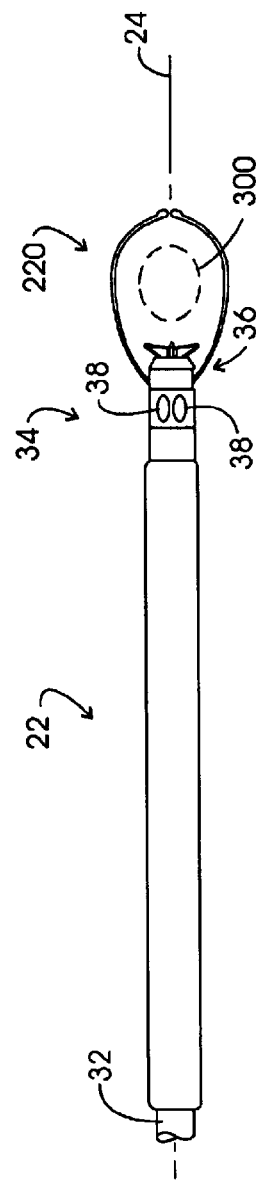
FIG. 13

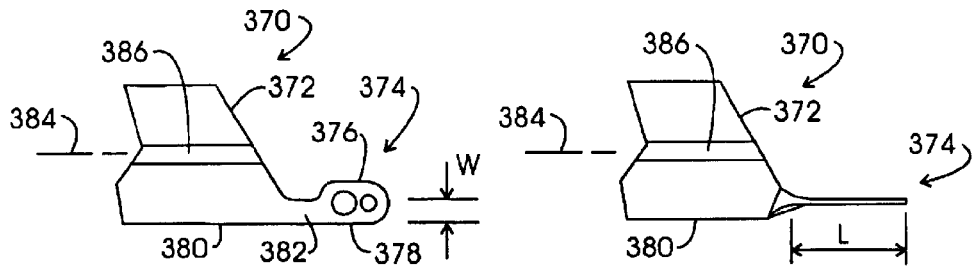
FIG. 14A
PRIOR ART
FIG. 14B
PRIOR ART
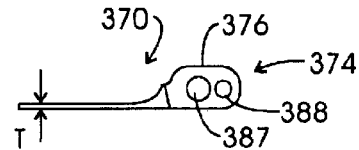
FIG. 14C
PRIOR ART
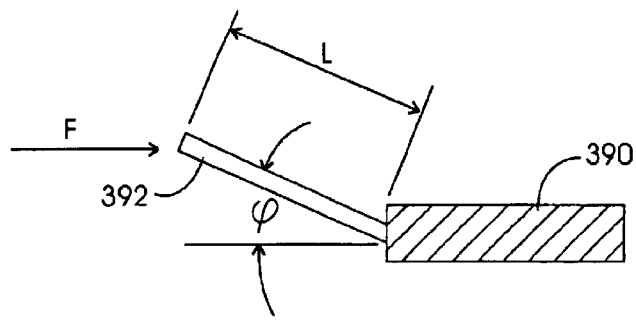
FIG. 15A
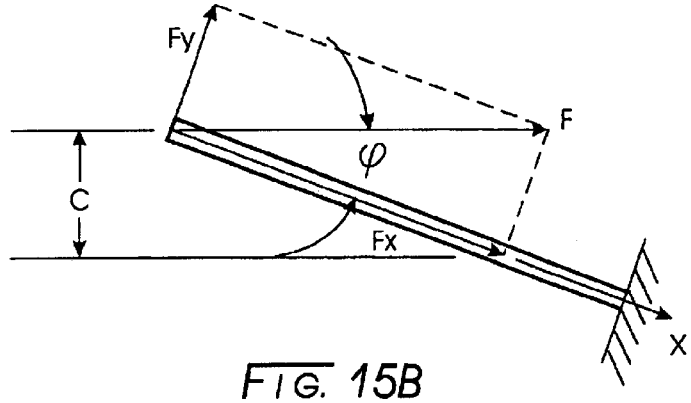
FIG. 15B

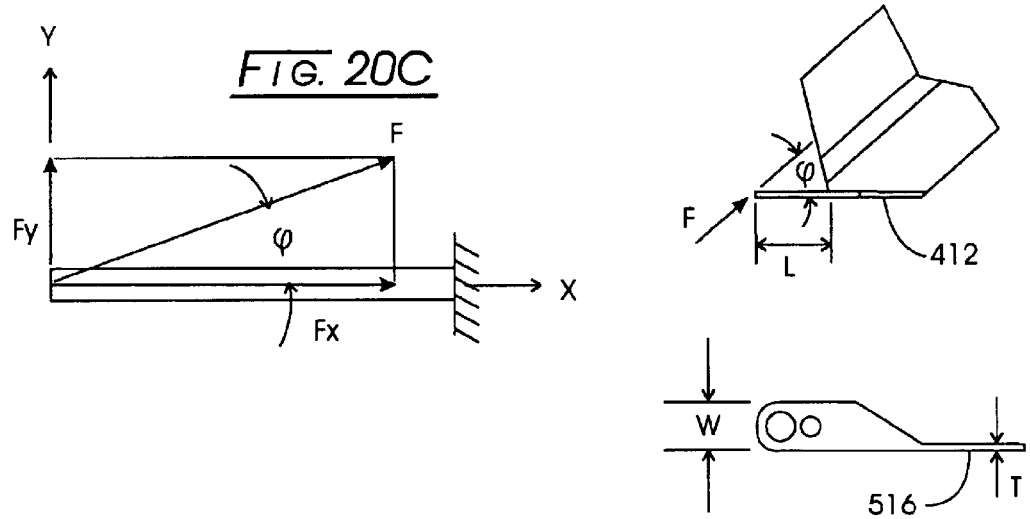
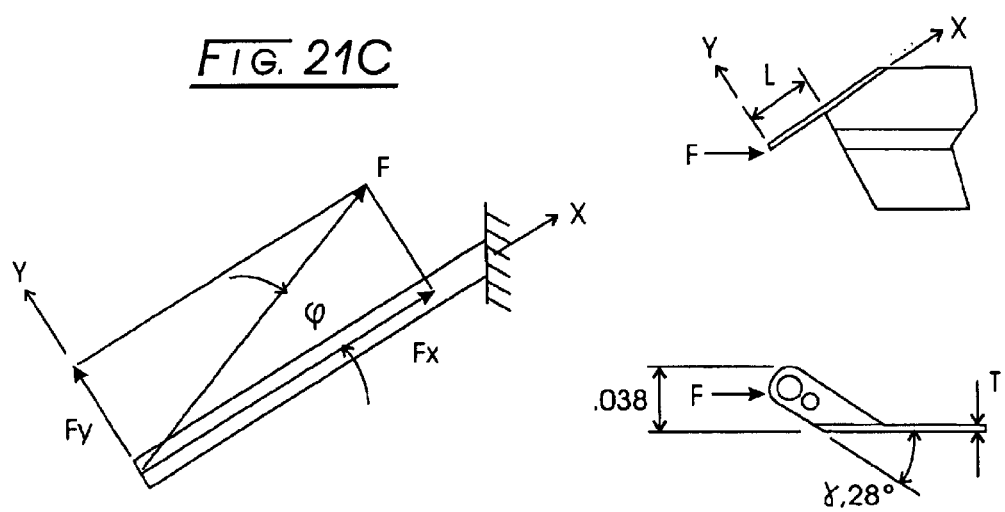

MINIMALLY INVASIVE INSTRUMENTATION FOR RECOVERING TISSUE

CROSS-REFERENCE TO RELATED APPLICATIONS

STATEMENT REGARDING FEDERALLY SPONSORED RESEARCH

Not applicable.

BACKGROUND OF THE INVENTION

The detection of tumorous lesions in the breast has progressed from early observation and palpation procedures to a variety of somewhat sophisticated imaging systems. A consequence of these advances in tumor detection is the identification of suspect tumor at an early stage in its development. Generally, at such early stages the suspect tumor may be somewhat small. Rather than resort immediately to an open surgical resection upon such early detection, practitioners generally carry out a preliminary, minimally invasive biopsy procedure. Such preliminary biopsy approaches are of importance, inasmuch as statistically, only 20% of these small tumors will be found to be malignant. Tumors determined to be benign have been left in situ with no excision. Over one million of these biopsies are performed in the United States each year, the procedure providing for the removal of part or all the suspect tissue for pathology examination and diagnosis. See generally:

(1) Rosen, Paul Peter, "Rosen's Breast Pathology", Lippincott-Raven Publishers, Philadelphia, 1997 pp 837–858.

One of the minimally invasive options is needle biopsy which may be either fine needle aspiration (FNA) or large core. Fine needle aspiration (FNA) is a procedure in which a fine needle, for example, of 21 to 23 gauge, having one of a number of tip configurations, such as the Chiba, Franzeen or Turner, is inserted into the breast and guided to the tumor site. A vacuum is created and the needle moved up and down along the tumor to assure that it collects targeted cellular material. Generally, three or more passes will be made to assure the collection of sufficient sample. Then, the needle and tissue sample are withdrawn from the breast for analysis.

The resulting specimen is subject to cytologic assay. In this regard, cell structure and related aspects are studied. This analysis has been used to improve or customize the selection of chemotherapeutic agents with respect to a particular patient.

While a fine needle aspiration biopsy has the advantage of being relatively simple, there are some drawbacks associated with its use. With fine needle aspiration, there remains a risk of false-negative results, which most often occur in cases involving extremely fibrotic tumor. In addition, after the procedure has been performed there may be insufficient specimen material for diagnosis. Finally, with fine needle aspiration alone the entire area of suspect tissue is not removed. Rather fragmented portions of tissue are withdrawn which do not allow a more advanced pathological investigation.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through a needle by vacuum suction. These needles have been combined with biopsy guns to provide automated insertion that makes the procedure shorter and partially eliminates location mistakes caused by human error or lesion displacement. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples. However, they still do not provide optimum pathological information. For further information concerning needle biopsy procedures see the following:

(2) Parker, Steve H, "Needle Selection and Steriotatic Large-Core Breast Biopsy", *Percutaneous Breast Biopsy* Eds. Parker, et al, Raven Press, New York, 1993 pp 7–14 and 61–79.

A device, which is somewhere between a needle biopsy and open surgery, is referred to as the Advanced Breast Biopsy Instrumentation (ABBI). With the ABBI procedure, the practitioner, guided by appropriate imaging, removes a core tissue sample of 5 mm to 20 mm in diameter. While the ABBI has the advantage of providing a large tissue sample similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for ABBI is limited by the size and location of the tumor, as well as by the presence of very dense parenchyma around the tumor. See the following publications:

(3) Parker, Steve H., "The Advanced Breast Biopsy Instrumentation: Another Trojan Horse?", Am. J. Radiology 1998; 171:51–53.

(4) D'Angelo, Philip C., et al., "Sterotatic Excisional Breast Biopsies Utilizing The Advanced Breast Biopsy Instrumentation System", Am. J. Surg. 1997; 174: 297–302.

(5) Ferzli, George S., et al., "Advanced Breast Biopsy Instrumentation: A Critique", J. Am. Coll. Surg., 1997; 185:145–151.

Another biopsy approach has been referred to as the mammotome and the Minimally Invasive Breast Biopsy (MIBB). These devices carry out a vacuum-assisted core biopsy wherein fragments of suspect tissue are removed with an 11–14 gauge needle. While being less invasive, the mammatome and MIBB yield only a fragmentary specimen for pathological study. These devices therefore are consistent with other breast biopsy devices in that the degree of invasiveness of the procedure necessarily is counterbalanced against the need of obtaining a tissue sample whose size and margins are commensurate with pathology requirements for diagnosis and treatment.

A minimally invasive approach to accessing breast lesions wherein the lesion is partially removed or removed in its entirety for diagnostic as well as therapeutic purposes has been described in U.S. Pat. No. 6,277,083 by Eggers, et al., entitled "Minimally Invasive Intact Recovery Of Tissue", issued Aug. 21, 2001. The instrument described includes a tubular delivery cannula of minimum outer diameter, the tip of which is positioned in confronting adjacency with a tissue volume to be removed. Following such positioning, the electrosurgically excited leading edge of a capture component is extended forwardly from the instrument tip to enlarge while electrosurgically cutting and surrounding or encapsulating a tissue volume, severing it from adjacent tissue. Following such capture, the instrument and the encaptured tissue volume are removed through an incision of somewhat limited extent.

An improved design for this instrument, now marketed under the trade designation EN-BLOC® by Neothemia Corporation of Natick Mass., is described in U.S. Pat. No. 6,471,659 by Eggers, et al., entitled "Minimally Invasive Intact Recovery Of Tissue", issued Oct. 29, 2002. The EN-BLOC® instrumentation includes a tubular delivery cannula of minimum outer diameter, the tip of which is positioned in confronting adjacency with the target tissue volume to be removed. Such positioning is facilitated through the utilization of a forwardly disposed precursor electrosurgical electrode assembly. Located within the interior channel of this delivery cannula is a capture component configured with five relatively elongate thin leafs mutually interconnected at their base to define a pentagonal cross-sectional configuration. Each of the leafs terminates forwardly at a tip with a transversely bent eyelet structure. Slidably extending through each eyelet is an electrically conductive pursing cable of a pursing cable assembly, which extends to an attachment with another adjacent leaf tip. This cable extends rearwardly through a small guide tube attached to a leaf for connection with the slidable cable terminator component of a drive assembly. The drive assembly is driven forwardly by an electric motor through a translation assembly. By adjusting the location of a stop component, which engages the cable terminator component, the size of a captured specimen may be varied. For example, the device can be configured to recover tissue specimens of 10 mm, 15 mm, 20 mm or 25 mm effective maximum diametric extent. As the cable terminator component is pulled by the cable assembly into abutting engagement with the stop component, the cables are tensioned to draw the leaf eyelet structures together in a pursing action.

Cabling involved with this instrument must quite diminutive in size while retaining adequate tensile strength in the temperature environment of an electrosurgical cutting arc. That temperature has been computationally estimated as being between about 1400° F. and 1600° F. Heretofore, cable having a nominal diameter of 0.006 inch has been employed. Structured with nineteen type 304 stainless steel strands having a diameter of about 0.0012 inch, the cable exhibited that flexibility requisite for feeding through the capture component leaf eyelets while creating a leading edge cutting arc. While this electrosurgical cutting arc is present, the cables further must sustain not only stresses associated with the forward movement of the capture component, but also those loads imposed by the encapturing pursing activity during which the eyelets are drawn together to complete encapsulation of the tissue sample. That configuration at pursing completion has been referred to as a "basket". Maximum loads are sustained by the cables at the completion of pursing movement. At that point in time, there is no movement and no frictional loss component and the cables are called upon to sustain loads imposed by the motor drive of the instrument as it enters a stall status. The latter stall condition, developing a 130 milliamp current spike, is detected to terminate the capture sequence. Test based experience with the instrument has determined that the load carrying capability of this cable structure at the noted elevated temperatures may be exceeded. While greater tensile strength is called for, no substantial increase in strand and thus cable diameter can be made due to the necessity of achieving a sufficient flexure or play-out as the cables pass through the leaf tip eyelets. Thus, improved strength at high temperatures is required without a compromise of cable deployment characteristics. Unacceptable increases in cable diametric size also would increase the power required for electrosurgical cutting.

The tip located eyelet structures, have heretofore been formed integrally with the thin (0.003 inch) capture component leafs. Because it is necessary to twist the eyelet structures to achieve necessary cable play-out or deployment, the eyelet structures have been configured with a narrow neck portion of 0.020 inch width and an overall length of about 0.080 inch. With the arrangement, the eyelets were twisted at the neck portion. Test experience with the capture components utilizing compressed porcine tissue has determined that, where the retrieval procedures encounter very dense breast tissue, the eyelets may fail by folding back. This is particularly the case where the instruments are structured for larger capture diameters, i.e., in the range of from about 15 mm to about 25 mm.

BRIEF SUMMARY OF THE INVENTION

The present invention is addressed to apparatus for electrosurgically cutting about a tissue volume. Looking to minimally invasive devices incorporating tissue retrieval features, cable manipulating eyelet structures are employed at the tips of multiple leaf assemblies which are capable of withstanding bending stresses imposed during cutting movement through dense tissue. Formed integrally with these leaf assemblies, and retaining their thickness, the eyelet structures are twisted or bent into perpendicularity with respect to the faces of an associated leaf. While exhibiting increased but constant widthwise dimensions with minimized lengths, the structures remain desirably small in size but exhibits substantially improved structure integrity when subjected to surgical activity within the environment of very dense tissue.

As another object and feature of the invention, the performance of tissue retrieving capture component cable assemblies is substantially improved in terms of tensile strength at the very high temperature environment associated with a cable supported electrosurgical cutting arc. Such performance not only requires improved tensional strength at high temperature, but also requires the maintenance of proper mechanical deployment characteristics. This latter requirement essentially precludes substantial increases in nominal cable diameter. The improved strength at higher temperatures is achieved by employing cable with strands of only about a 1.4 mil diameter formed, for instance, of a type 316 stainless steel. Such improved strength is at an unexpected level. Published tensile strength at high temperature data for the type 316 material indicates only about a 30% strength improvement over type 304 stainless steel which was earlier employed to form the cable strands. However, the cable formed with type 316 stainless steel has been determined to be more than 104% stronger (a factor of 2.04) than the earlier multi-strand cable formed with type 304 material.

Other objects of the invention will, in part, be obvious and will, in part, appear hereinafter. The invention, accordingly, comprises the apparatus possessing the construction, combination of elements and arrangement of parts which are exemplified in the following detailed description.

For a fuller understanding of the nature and objects of the invention, reference should be made to the following detailed description taken in connection with the accompanying drawings.

BRIEF DESCRIPTION OF THE DRAWINGS

FIG. 4 is a side view showing a capture component employed with the instruments of the invention illustrating it's structure at a stage of production;

FIG. 5 is a sectional view of a completed capture component;

FIG. 6A is a plan view of the forward region of a leaf of the capture component of FIG. 4;

FIG. 6B is a plan view of the forward tip region of the leaf shown in FIG. 6A but with it's eyelet structure twisted to perpendicularity with respect to a leaf face;

FIG. 6C is a side view of the tip region shown in FIG. 6B;

FIG. 7 is a sectional view of a leaf of a capture component according to the invention;

FIG. 8 is a partial sectional view of the forward region of the disposable component of the instrument of FIG. 2;

FIG. 12 is a partial sectional view of the instruments of FIG. 11 showing a deployment of capture component leafs to a maximum diametric extent;

FIG. 13 is a partial sectional view of the instrument of FIG. 11 showing the orientation of the capture component leafs and associated drive components at a completion of capture of a tissue volume;

FIG. 14A is a plan view of the tip region of a capture component leaf according to the prior art and showing it at a stage of formation;

FIG. 14B is a plan view of the tip region of a capture component leaf showing eyelet structure twisted into perpendicularity with respect to a face of the leaf and being formed in accordance with the prior art;

FIG. 14C is a side view of the tip region shown in FIG. 14B;

FIGS. 15A and 15B are a force analysis model of the eyelet structure shown in FIG. 6A-6C, FIG. 15A showing the geometry employed for analysis and FIG. 15B showing a force diagram;

FIGS. 20A–20C combine to provide a force analysis model with respect to the eyelet structure shown in FIG. 16, FIGS. 20A and 20B showing geometric attributes and FIGS. 20C providing a force diagram;

FIGS. 21A–21C combine to provide a force analysis model with respect to the eyelet structure shown in FIGS. 17 and 18, FIGS. 21A and 21B showing geometric attributes and FIG. 21C providing a force diagram;

DETAILED DESCRIPTION OF THE INVENTION

In the discourse to follow, computational data as well as test data taken with breast phantom materials are set forth. These data materials were developed in conjunction with investigations carried out with the noted tissue retrieval system marketed under the trade designation EN-BLOC®. Accordingly, that system is initially described.

Figure 1:
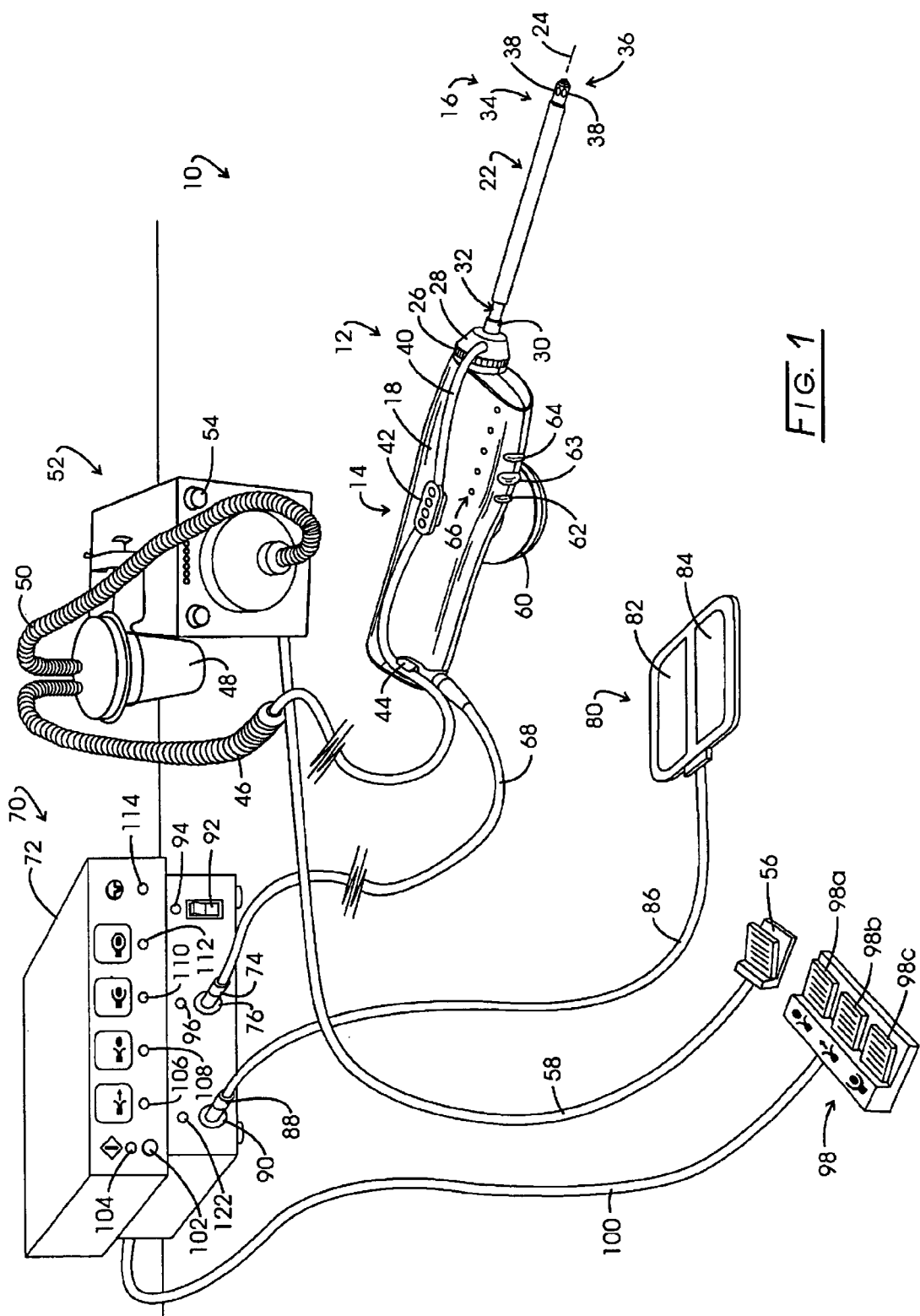
FIG. 1 is a perspective view of an electrosurgical system employed incorporating the apparatus of the invention.

Referring to FIG. 1, the noted system for isolating and retrieving a target tissue volume or biopsy sample is illustrated in general at 10. System 10 comprises a tissue retrieval instrument represented generally at 12 which includes a reusable component represented generally at 14, sometimes referred to as a "handle". Instrument 12 additionally includes a disposable component represented generally at 16, the rearward portion of which is removably mounted within the polymeric housing 18 of reusable component 14. The disposable component 16 is sometimes referred to as a "probe".

Disposable component 16 includes an elongate cannula assembly or support member represented generally at 22 which extends along an instrument axis 24. The proximal end of cannula assembly 22 extends through a rotatable, externally threaded connector 26. Connector 26 is threadably engaged within the housing 18. Cannula assembly 22 additionally extends through a rotatable suction manifold 28 which is a component of an evacuation system. Manifold 28 is retained in position on cannula assembly 22 by a ferrule or collar 30 which is mounted over the outward surface of a tubular cannula component, a portion of which is represented at 32. Most of the outward surface of the cannula assembly 22 will be seen to be covered with an electrically insulative thin polyolefin shrink-wrap or tube. The forward region of the cannula assembly 22, as represented generally at 34 extends to a distal end or tip represented generally at 36. Suction or vacuum manifold 28 is in vacuum conveying and fluid receiving relationship through cannula assembly 22 with four intake ports located at the forward region 34, two of which are shown at 38. The evacuated fluids will be at an elevated temperature due to the electrosurgical nature of the instrument 12 and will include steam, smoke and liquids such as blood and accumulations of local anesthetic. Vacuum is conveyed to and this noted elevated temperature fluid is received from suction manifold 28 via a flexible transparent polymeric tube 40. Tube 40 extends from an evacuation outlet (not shown) at manifold 28 into press-fit connection with connectors 42 and 44, whereupon it is coupled with a flexible tube or hose of larger diametric extent shown at 46. Hose 46 extends to a fluid trap and filter assemblage 48 which is in vacuum communication via flexible hose 50 with the suction input of a suction pump assembly represented generally at 52. Vacuum or suction pump assembly 52 may be of a type marketed under the trade designation "VersaVac 2" by Stackhouse, Inc. of Palm Springs, Calif. Pump assembly 52 may be actuated into operation from a switch arrangement shown, at 54 or through utilization of a footswitch 56 coupled to the pump assembly 52 via a cable 58.

Connectors as at 42 are positioned on each side of the housing 18 and function additionally to support a stabilizer hand grip, for example, the annulus-shaped grip represented at 60. Connectors as at 42 also may be employed to support the instrument 12 for stereotactic manipulation. Positioned at the forward portion of the housing 18 are three button switches 62–64 which function, respectively as an arm/disarm switch; an energize/position switch; and a start tissue capture switch. Immediately above the switches 62–64 on each side of housing 18 are linear arrays of light emitting diode (LED) based indicator or cueing lights, one such array being represented generally at 66. The visual cues provided by the indicators at 66, from the forward region of housing 18 toward the rear region thereof, provide a start/reset cue as a green light; a tissue capture complete cue provided as a green light; a start tissue capture cue (above switch 64) provided as a yellow light; an energize/position cue (above switch 63) provided as a yellow light; and an arm/disarm cue (above switch 62) provided as a green light. Energization and electrical control is provided to the instrument 12 via a multi-lead cable 68 which connects with a combined control assembly and electrosurgical generator represented generally at 70 and incorporated within a console 72. The device 70 is provided as a model "3000 RF Controller" marketed by Neothermia Corporation (supra). Connection of the cable 68 with the console 72 is shown at a multi-lead connector 74 which is coupled to a console connector 76. The electrosurgically active electrode assembly of the instrument 12 performs in monopolar fashion. Thus, a conventional, relatively large, dispersive return electrode assembly as shown in general at 80 is positioned against the skin surface of the patient. Assembly 80 is configured as having two electrode components 82 and 84 which are connected via cable 86 and connector 88 to console connector 90. Alternately, a return electrode may be positioned at the surface of cannula assembly 22 near its distal end in place of the illustrated use of a dispersive return 80.

Power is supplied to the circuitry at console 72 upon actuation of an on/off switch 92. When switch 92 is in an "on" orientation, a green visual indicator LED 94 located above the switch is energized. Proper connection of the cable 68 and connector 74 with console connector 76 is indicated by an illuminated green LED 96 positioned above connector 76. This connection test is carried out by directing current to a coding resistor within housing 18. A three-pedal footswitch represented generally at 98 is coupled via a cable 100 to the rear panel of console 72. The three pedals, 98a–98c of switch 98 emulate and provide alternative switching with respect to button switches 62–64.

Visual cueing corresponding with that at housing 18 LED arrays as at 66 also is provided at the console 72. In this regard, a start/reset switch 102 is operationally associated with an LED indicator 104 which illuminates in a green color upon actuation of that switch. An energize/position mode visual cue LED representing an energization of a precursor electrode assembly at tip 36 is shown at 106. This LED provides a yellow output during the electrosurgical advancement of cannula assembly tip 36 into confronting adjacency with a targeted tissue volume. Next, a green, arm/capture mode visual cue is provided by an LED 108 to represent an arming of the tissue capture feature of instrument 12. Once an arm/disarm switch as at 62 or 98a is depressed, the energize/position switches as at 63 or 98b are no longer activatable. However, the practitioner may return to the positioning mode by again depressing an arm/disarm switch. A yellow capture mode visual cue is provided by an LED 110 to represent the start of and carrying out of a tissue capture or retrieval procedure and upon completion of such capture, a green capture complete mode visual cue is provided by a green LED 112. A pause mode condition is represented by the energization of a green LED 114. In general, the pause mode is entered during a procedure by releasing capture switch 64 or footswitch 98c. When in a pause mode, the active capture electrodes of the instrument 12 are not energized and deployment of its capture component is halted. However, the evacuation function carried out by the suction pump assembly 52 continues to perform. To reenter the capture mode, the practitioner again depresses footswitch 98c or capture switch 64. Upon such re-actuation of the chosen switch, the capture mode continues, in effect, from the orientation where it left off. This pause mode of operation of the system may be employed by the practitioner during a capture mode of operation to permit, for example, the evacuation of fluids encountered by arc-based cutting components. Such fluids may, for example, be accumulations of local anesthetic solution, blood or the like.

An assurance that the vacuum system is operating, at least to the extent that the vacuum pump assembly 52 is active, can be accomplished with a vacuum actuated switch (not shown) attached with the conduiting extending between the pump assembly 52 and the instrument 12. For example, unless such a switch is actuated, the commencement of a procedure can be logically blocked by the control assembly 70. In addition to the removal of smoke and such fluids as are discussed above, the evacuation system, including pump assembly 72 and conduiting defining a transfer channel extending to the intake ports 38, functions to remove steam which is generated by the encounter of an electrosurgical cutting arc with fluid of tissue cells. This removal of steam (as a component of elevated temperature fluid) serves, inter alia, to protect healthy tissue surrounding the region of cutting from thermal trauma.

At the time the connector 88 of return electrode 80 is coupled to console connector 90 and switch 92 is in a power-on condition, a patient circuit safety monitor (PCSM) carries out a self test. On subsequent actuation of the start/reset switch 102, a fault test with respect to the two electrode components 82 and 84 is performed. In the event the latter test fails, then both visual and aural pulsating warning cues are activated, the visual cue being provided at a red LED 122 located adjacent connector 90.

Figure 2:
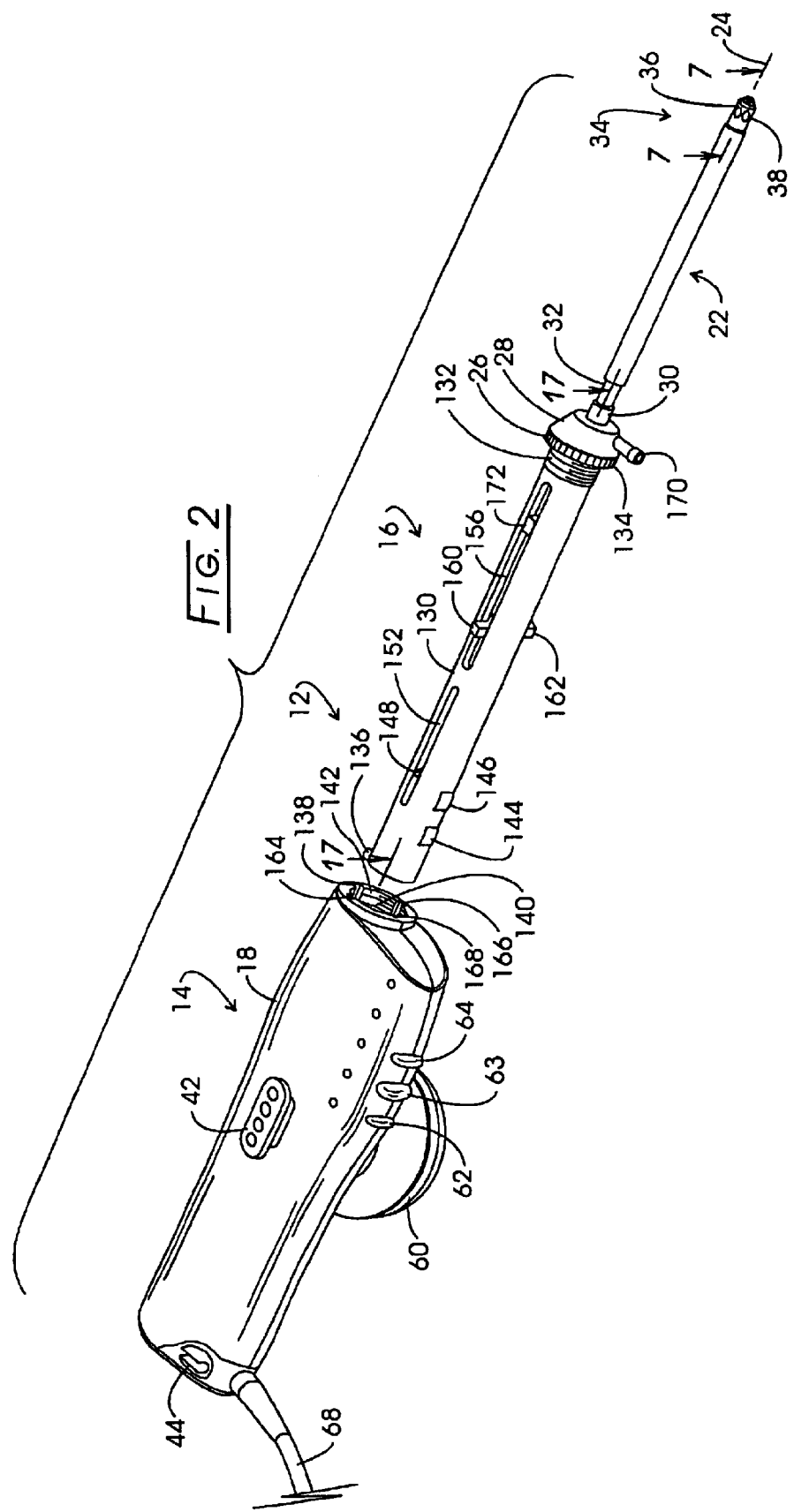
FIG. 2 is an exploded view of an electrosurgical instrument shown in FIG. 1.

Referring to FIG. 2, the disposable component 16 of instrument 12 is revealed in an orientation prior to its insertion within the housing 18 of reusable component 14. In the figure, cannula assembly 22 is seen extending forwardly from a cylindrically-shaped support housing 130. The forward region of support housing 130 supports the rotatable connector 26. In this regard, it may be observed that the connector 26 is configured with external threads 132 which are fixed for rotation with a grasping surface 134 formed with spaced indentations to facilitate its hand rotation. At the rearward end of support housing 130 there is located an upstanding indexing pin 136 which, during installation of the disposable component 16, is slidably received within an upwardly disposed elongate slot 138 extending internally along an elongate receiving cavity 140. Internal threads 142 within cavity 140 threadably engage the external threads 132 of connector 26 when the disposable component 16 is mounted with the reusable component 14.

Positioned opposite indexing pin 136 on support housing 130 are two, spaced apart electrical contacts 144 and 146 which are oriented to make wiping contact with corresponding electrical terminals disposed within housing 18 upon insertion of support housing 130 within the receiving cavity 140. Contacts 144 and 146 selectively receive electrosurgical cutting current which is applied respectively to a precursor electrode assembly at tip 36 and the electrosurgical cutting and pursing cables associated with a capture component initially retained within cannula assembly 22. Those pursing cables extend from the capture component within cannula component 32 to a cable terminator component having guidance tabs or ears, one of which is revealed at 148 slidably mounted within an elongate stabilizer slot 152 arranged in parallel with axis 24. A corresponding guidance tab and slot combination is found at the opposite side of support housing 130. Located forwardly of the slots as at 152 are two elongate drive slots, one of which is shown at 156 similarly arranged in parallel with axis 24. The outwardly extending ears or guide tabs of a drive assembly drive member extend from these slots and are seen at 160 and 162. These ears or tabs 160 and 162 support rearwardly disposed driven surfaces which are used to impart forward movement to drive assembly components. This forward movement functions to deploy the noted capture component from cannula component 32. When the support housing 130 is installed within the receiving cavity 140 of housing 18, these tabs 160 and 162 pass through oppositely disposed notches shown respectively at 164 and 166 provided at a forward portion of housing 18. Similarly, a notch 168 is located forwardly within housing 18 to permit passage of the electrical terminals 144 and 146.

The procedure for installing the disposable component 16 within reusable component 14 involves the sliding of support housing 130 within the receiving cavity 140 and rotating grasping surface 134 of connector 26 to provide for the engagement of threads 132 with threads 142. Upon completing the assembly, the flexible transparent tube 40 of the evacuation assembly may be attached to an evacuation outlet 170 depending outwardly and in fluid and suction or vacuum communication With suction manifold 28. Finally, a tab at 172 is seen extending through a forward portion of the drive slot 156. This tab may be a component of a drive assembly safety stop functioning to limit the extent of forward travel permitted by the drive member component having the ears 160 and 162. It is located in accordance with a preselected capture component maximum effective diametric extent. Such a tab also may function as a capture complete stop which serves in the derivation of a capture complete signal derived as the current spike witnessed upon a stall of an electric drive motor. That signal is conveyed to control assembly 70.

Figure 3:
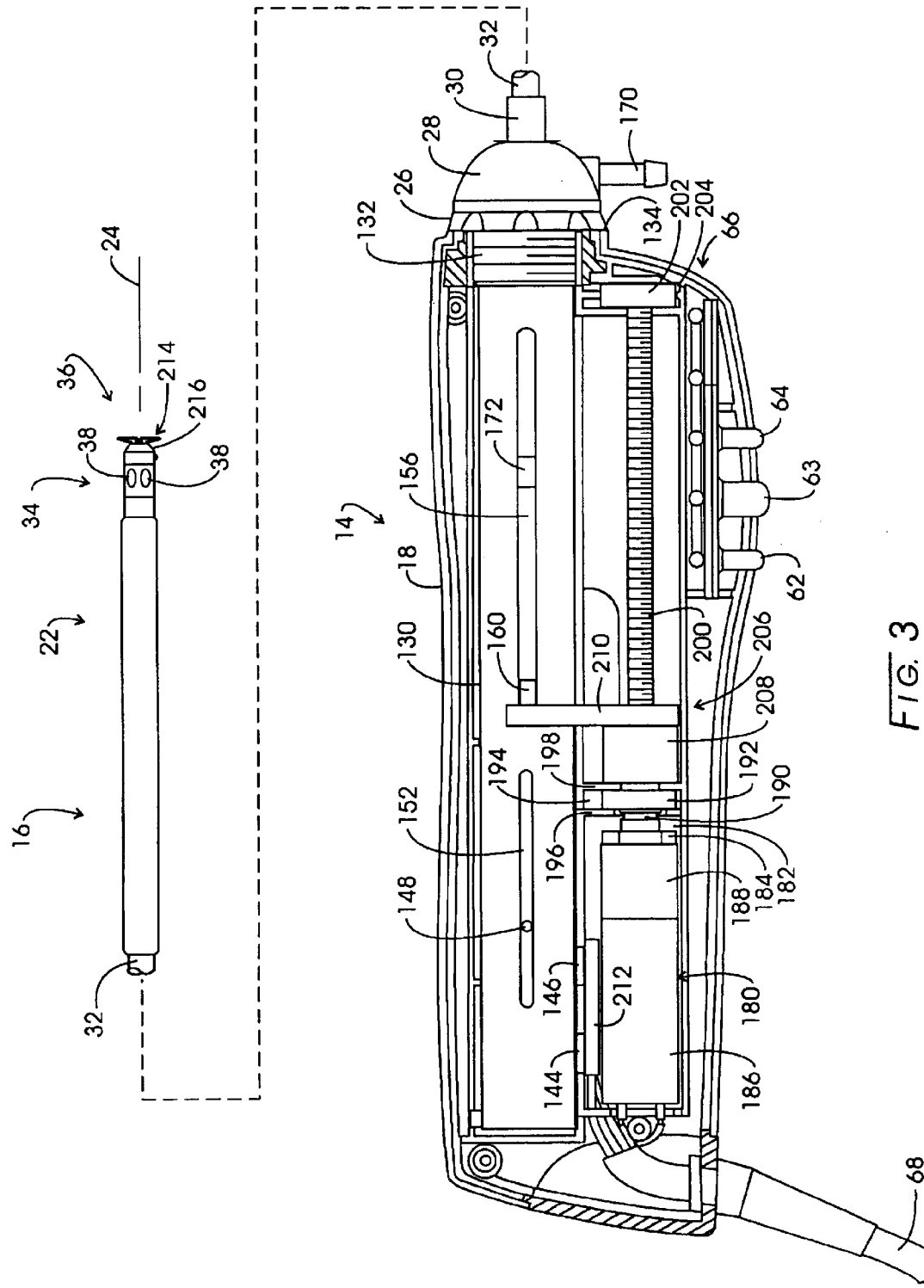
FIG. 3 is a partial sectional view of the instrument shown in FIG. 2 with portions broken away.

Referring to FIG. 3, a sectional view is presented illustrating the operative association of motor drive features of the reusable component 14 with the support housing 130 of disposable component 16. In the figure, a motor assembly represented generally at 180 is seen to be located within a motor mount chamber 182. In that chamber 182 the motor assembly 180 is permitted some self-aligning movement but is restrained from rotational movement by a torque stop component 184. Motor assembly 180 incorporates a motor component 186 which is coupled in driving relationship with a planetary gear assembly 188. The drive output of the planetary gear assembly 188 is connected in driving relationship with a stainless steel flexible bellows-shaped coupler 190 which extends through a fluid seal 192 located within a seal chamber 194 defined by oppositely disposed and spaced apart bulk-heads 196 and 198. Seal 192 does not constrain the coupler 190 and permits the noted self-alignment of the motor assembly 180 with respect to its coupling to a rearward end of an elongate threaded translation component 200. The forward end of translation component 200 extends into engagement with a thrust bearing 202. Bearing 202 provides support against all of the driving forces imposed from the motor assembly 180, and is mounted and secured within a thrust bearing chamber 204. Translation component 200 is threadably engaged with a transfer assembly represented generally at 206 which comprises a ball screw or nut component 208 and a generally Y-shaped yoke 210 which is configured to extend to a position aligned for driven but freely abutting engagement with the tabs or ears 160 and 162 (FIG. 2). During a capture procedure, the translation component 200 is drivably rotated in an appropriate direction to move the transfer assembly 206 forwardly. That movement, in turn, urges a drive component forwardly until capture component pursing activity is completed and motor component 186 enters a stall condition. At that juncture, the control system 70 halts electrosurgical cutting current and reverses the directional drive sense of motor 186 to cause the transfer assembly 206 to return to a "home" position generally illustrated in the instant figure. The figure additionally reveals that the two electrical contacts 144 and 146 located upon support housing 130 will be in contact with corresponding contacts (not shown) supported by a polymeric contact clamp 212.

FIG. 3 also reveals some details of the tip 36 of the cannula assembly 22. The tip incorporates four precursor electrode components arranged in a cross-shape or symmetrically about instrument axis 24 as is represented in general at 214. These precursor electrodes are located just forwardly of a truncated cone-shaped ceramic (alumina) protective tip component 216. Tip component 216 functions to provide an arc-resistant or arc isolating tip portion preventing its breakdown.

A more detailed description of the system 10 including the control assembly 70 and the drive system within housing 18 is provided in the above-referenced U.S. Pat. No. 6,471,659 which is incorporated herein by reference.

The forward drive movement of transfer assembly 206 by motor assembly 180 and translation component 200 serves to impart forward drive to a drive member within cylindrical support housing 130 which, in turn, drives forwardly a drive tube functioning to deploy a capture component, the leading edge of which is provided as a pursing cable assembly having an initially expanding and then contracting effective diametric extent which circumspectively cuts around a target tissue volume and thus encapsulates a resultant tissue sample for removal.

Referring to FIG. 4, this capture component which is retained within the internal structure of cannula component 32 prior to its deployment is represented in general at 220 at a stage in its fabrication prior to the attachment of pursing cables and associated polymeric guide tubes for those cables. Component 220 is formed by chemically milling flat type 304 stainless steel sheet stock to provide for the formation of a pentagonal base portion represented generally at 222 which is weldably attached to the above-noted drive tube represented at 224. Drive tube 224 extends through the cannula component 32 and into the interior of cylindrical housing 130 (FIG. 2). Formed integrally with the base portion is a leaf assembly represented generally at 226. Looking additionally to FIG. 5, the sleeve assembly is seen to be comprised of leafs 228–232, a bending notch being chemically milled to define these leafs within the base portion 222 and each leaf having a chemically milled groove extending along its centrally disposed leaf axis. Such a leaf axis is seen in FIG. 4 at 234 with respect to leaf 228. Axis 234 extends to a tip region, for instance, that shown at 236 with respect to leaf 228. Looking additionally to FIG. 6A, tip region 236 of leaf 228 reappears at the noted stage of fabrication. The region 236 extends to a forward edge 238 which is seen to taper or slant inwardly toward the base portion 222 from a location of adjacency at 240 with the eyelet edge 242 of an eyelet structure represented in general at 244a. Leaf edge 238 slants at an angle of 53.5° with respect to leaf axis 234. Eyelet structure 244a is seen to be formed having a cable-receiving aperture 246a as well as a cable tie-off aperture 248a positioned inwardly therefrom. Eyelet structure 244a extends in a widthwise sense from eyelet edge 242 to an oppositely disposed eyelet edge 252 to define a substantially constant width, W, (see FIG. 6C). Edge 252 is seen to be aligned and configured as an extension of a leaf side edge 254. Edge 254 is spaced from opposite leaf side edge 256 to define a leaf width. Note additionally, the presence of a centrally disposed chemically milled groove 258a.

Referring to FIGS. 6B and 6C, leaf 228 is seen to have a thickness, T, extending between its oppositely disposed leaf faces 260 and 262. As a subsequent step in fabrication, the eyelet structure 244a is seen to be twisted such that its surfaces are substantially perpendicular to the leaf faces 260 and 262. Note in FIG. 6B that this twisting incorporates a portion of the leaf tip region 236 to achieve structural buttressing. FIG. 6C further reveals that the eyelet edges 242 and 252 are parallel with the planes represented by leaf faces 260 and 262, leaf edge 242 extending below the plane of leaf face 262. Note, additionally, that the planes in which each surface of the eyelet structure 244a resides are parallel with the leaf axis 234 when twisted into the orientation shown in FIGS. 6B and 6C. This twisting activity tends to align the eyelet with leaf axis 234. During assembly of probe 16 eyelet structure 244a, when a manual capture test is performed, will be bent slightly toward axis 234.

Returning to FIG. 5, within each leaf 228–232 there is chemically milled the noted groove as described in FIGS. 6A–6C at 258a. The remaining grooves are identified at 258b–258c. For the instant embodiment, those grooves function to aid in the support of a flexible polyamide guide tube which functions as a cable guide channel extending centrally along the lengthwise extent of the leafs to terminate in a guide outlet located along each leaf axis as at 234 and spaced inwardly from the edges as at 238. This geometry facilitates the dynamic passage of the pursing cables from the guide outlet and thence through the cable receiving apertures as described at 246a in connection with leaf 228. The guide tubes, which are illustrated in connection with FIG. 5 are quite small having, for example, an outside diameter of about 0.020 inch and a wall thickness of about 0.0015 inch. Such guide tubes are shown in the figure at 268–272 as being adhesively attached to respective leaf grooves 258a–258e. Each of the guide tubes 268–272 slidably guides a pursing and cutting cable as shown respectively at 278–282. These 19-strand cables are formed of a type 316 stainless steel and exhibit, when combined or braided, a nominal diameter of about 0.006 inch. The corresponding strand diameters will be about 1.2 mils for that cable diameter. This sizing of the cables is determined with respect to maintaining requisite strengths at electrosurgical excitation temperatures which, as noted above, have been computationally determined to range from about 1400° F. to about 1600° F. These cable components further must retain a capability for readily "playing out" or passing through the cable receiving apertures of the eyelet structures during the initial phase of target tissue capture and, in effect, reversing during the final interval of capture. Polyamide guide tubes 268–272 are attached to the chemically etched grooves 258a–258e within the leafs by initially adhesively coupling them to the grooves. Then, each tube is fixed to a corresponding leaf within the chemically milled groove utilizing an electrically insulative coating material and process which achieves bonding and provides requisite electrical insulation for the entire capture component.

Looking to FIG. 7, that insulative coating is shown at 284 in connection with a sectional view of leaf 228 and associated polyamide tube 268. Coating 284, which has a thickness of about 0.001 inch, is a vapor phase polymerized conformal coating marketed under the trade designation "Parylene". Parylene is the generic name for members of a polymer series. The basic member of the series, called Parylene C is a poly-para-xylene, a completely linear, highly crystalline material. Such coatings are available from Parylene coating service companies such as Specialty Coating Systems, of Indianapolis Ind. Leafs 228–232 are formed having a thickness, T, preferably of 0.003 inch and a widthwise extent, for example, between leaf side edges 254 and 256 of 0.080 inch. However, this thickness may range from about 0.0025 inch to about 0.005 inch.

Referring to FIG. 8, a sectional illustration of the forward region 34 and tip 36 of the cannula assembly 22 is provided. Tip 36 is depicted as it is utilized for capturing tissue volumes having a principal effective diametric extent of, for example, extending from about 10 mm to about 20 mm. The tip 36 incorporates four precursor electrode components arranged in quadrature or cross-shaped symmetrically about instrument axis 24. Three of the elongate generally L-shaped precursor electrodes are revealed at 290–292. When electrosurgically excited by actuation of either switch 63 or 98a, the forward surfaces of the stainless steel wire electrodes function to support a cutting arc. Those forward precursor electrode components are, in turn, located just forwardly of the truncated cone-shaped protective tip 216. Mounted rearwardly of the tip component 216 are polymeric tip components 294 and 296, these components functioning to provide a ramp structure through which the leafs of the capture component 220 may extend. In this regard, leaf 228 with its associated eyelet structure 244a is seen in its retracted position. When urged forwardly by the above-noted drive rod 224, these leafs will slidably extend forwardly at an attack angle of about 45° until reaching a location of maximum effective diametric extent about one half way along their longitudinal locus of travel. This locus of travel is schematically represented in dashed fashion at 298 in conjunction with a symbolic target tissue volume 300. When approaching the noted halfway point in a capture sequence, the pursing cables will commence to draw the eyelet structures together to converge at instrument axis 24. Such pursing activity is initially modulated by progressively developed cable leads and then is carried out relatively rapidly to somewhat emulate the cutting profile of initial deployment. The capture may retrieve all or a sample of a tissue volume. The structure of the cannula assembly 22 looking inboard from cannula component 32 at forward region 34 is seen to include capture component leafs, two of which are represented at 228 and 231. Next inwardly inboard is a stainless steel support tube 302 which is mounted at the rear portion of support housing 130 of disposable component 16 and extends forwardly through cannula component 32 to a flared region 304 engaging polymeric tip component 294. This flaring is found to be helpful in permitting the support tube to overcome the rather substantial forwardly directed forces occurring during forward deployment of the capture component leafs and cables. Note additionally, that the somewhat annular space between the wall of cannula component 32 and support tube 302 provides the earlier-noted evacuation system transfer channel diverting elevated temperature fluid. That transfer channel is represented at 306. Channel 306 extends from the intake ports 38 at forward region 34 to suction manifold 28 and its associated evacuation outlet 170 (FIG. 2).

Located inside support tube 302 is an electrosurgical precursor electrode tube 308 which also extends to the rearward portion of support housing 130 for purposes of both support and receiving electrosurgical cutting energy transmitted through electrical contact 144 (FIG. 2). As the precursor electrode tube 308 extends rearwardly, it is electrically insulated from support tube 302 by a polymeric (polyolefin) shrink-wrap 310.

The precursor electrodes are mounted as a subassembly of four stainless steel electrode wires having the noted generally elongate L-shape as seen, in particular, at 290 and 291 in the instant figure. Elongate components of the precursor electrodes, for example, as identified at 312 and 314 with respect to electrodes 290 and 291 extend into a subassembly tube 316. Four such electrode assemblies are crimped inside of this tube 316 and that tube, 316, in turn, is crimped within the forward portion of the precursor electrode tube 308.

Figure 9:
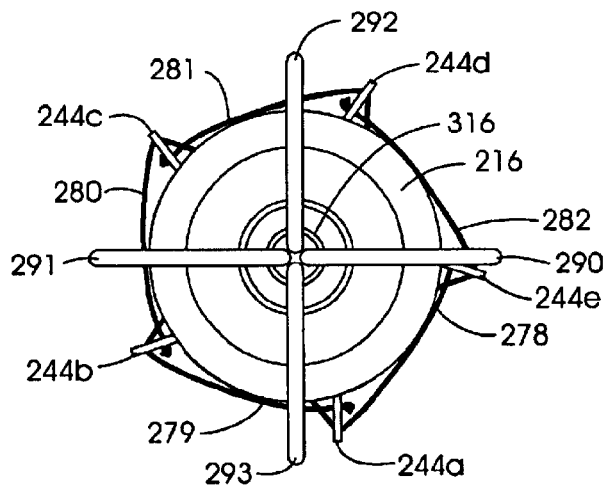
FIG. 9 is a front view of an instrument according to the invention showing a capture component in a retracted orientation.
Figure 10:
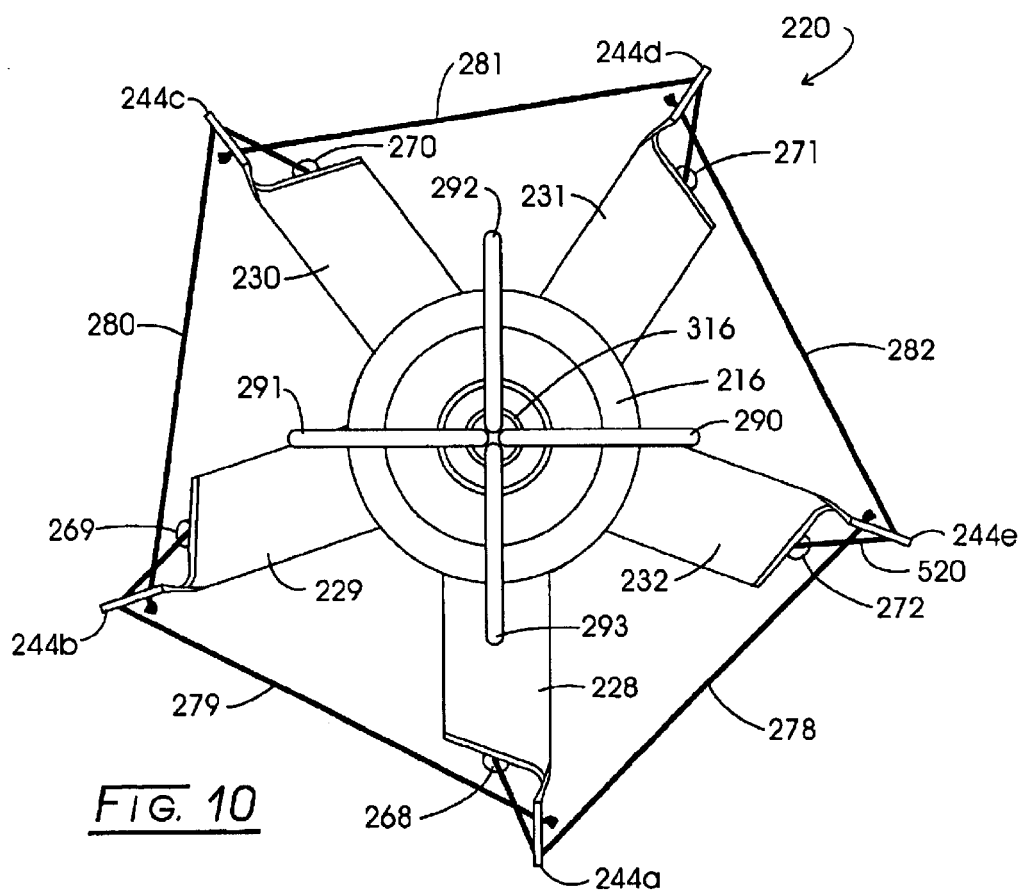
FIG. 10 is a front view of the instrument of FIG. 9 showing the capture component thereof at a stage in its deployment.

Referring to FIGS. 9 and 10, frontal views of the precursor electrodes 290–293 are revealed. In general, the precursor electrodes 290–293 will have a tissue cutting and confronting length of about 6.5 mm to about 7.0 mm for employment with instruments configured to develop a maximum effective capture diameter for the capture component 220 of about 10 mm to about 20 mm. Where that maximum effective diameter expands above about 20 mm up to about 40 mm, the corresponding expanse of the precursor electrodes or their lengthwise confronting extent will be about 10 mm to about 15 mm. When configured having one of the larger lengthwise extents, the electrodes are slightly canted forwardly and are made resilient so as to be capable of flexing forwardly as the electrosurgically excited pursing cables physically contact the precursor electrodes. During this procedure, the precursor electrodes are open-circuited and permitted to be re-energized as they are urged into alignment with the capture component leafs. This temporary re-energization of the longer precursor electrodes is found to be beneficial as the electrodes retract or bend toward the target tissue sample being captured.

FIGS. 9 and 10 additionally present front views of the cannula assembly 22 forward region further illustrating the capture component 220 leaf, cabling and eyelet structures. In this regard, those cables and leafs are illustrated in a retracted state in FIG. 9, eyelet structure 244a reappearing from FIGS. 6B and 6C and the remaining eyelet structures being identified at 244b–244e. In contrast, FIG. 10 shows an orientation of the leafs and cables as they are being deployed toward their maximum effective diametric extent. FIG. 10 reveals that cable 278 emerges from guide tube 268 to pass through the cable-receiving aperture of eyelet structure 244a and extends to a knotted connection with eyelet structure 244e of leaf 232. Similarly, cable 279 extends from guide tube 269, passes through eyelet structure 244b and is tied-off at eyelet structure 244a. Cable 280 emerges from guide tube 270 at leaf 230, extends through eyelet structure 244c and is tied-off at eyelet structure 244b. Cable 281 emerges from guide tube 271, extends through eyelet structure 244d and is tied-off at eyelet structure 244c. Lastly, cable 282 emerges from guide tube 272 at leaf 232, passes through the cable-receiving aperture of eyelet structure 244e and is tied-off at eyelet structure 244d.

FIG. 10 depicts the capture component 220 in an orientation wherein it is at the halfway point along its forwardly directed locus of travel. As it approaches this position in the procedure, the pursing cables will have been played out from the guide outlets of the guide tubes and through an associated cable-receiving aperture at an eyelet structure. The geometric relationship between the guide outlet and that aperture is important to facilitate this cable movement. As the cables are tensioned to commence pursing activity, the eyelet structures 244a–244e will mutually converge toward instrument axis 24 and at full pursing, their greatest exposed length will be that which extends from a cable guide outlet to the associated cable receiving aperture, for example that portion of cable 282 extending from the outlet of guide tube 272 to the cable receiving aperture of eyelet structure 244e.

In general, within about three seconds following the commencement of the electrosurgical cutting procedure with either the precursor electrodes or the capture component, heat released, for example, from the arc generated steam which condenses within the transfer channel 306 will result in a latent heat of vaporization within that channel which will, in turn, elevate the temperature of the external surface of the wall of cannula component 32. Returning to FIG. 8, this surface heat phenomenon is seen to be accommodated for through the utilization of a thermally insulative sheath represented generally at 318. Sheath 318 is configured as a stainless steel tube or cylinder 320 having forward and rearward standoffs which are configured by rolling the cylindrical end of tube 320. The forward standoff is shown at 322. With this construction, an annular air gap or layer 324 is defined which provides thermal insulation. The figure further reveals that extending over the cannula component assembly 22 is an electrically insulative polyolefin shrink-wrap or shrink tube 326. Polyolefin wrap 326 has a thickness of about 0.003 inch. Note that it extends to a forward terminus 328. The gap provided at air layer 324 by the tube 320 is about a 0.017 inch annulus-shaped spacing.

Figure 11:
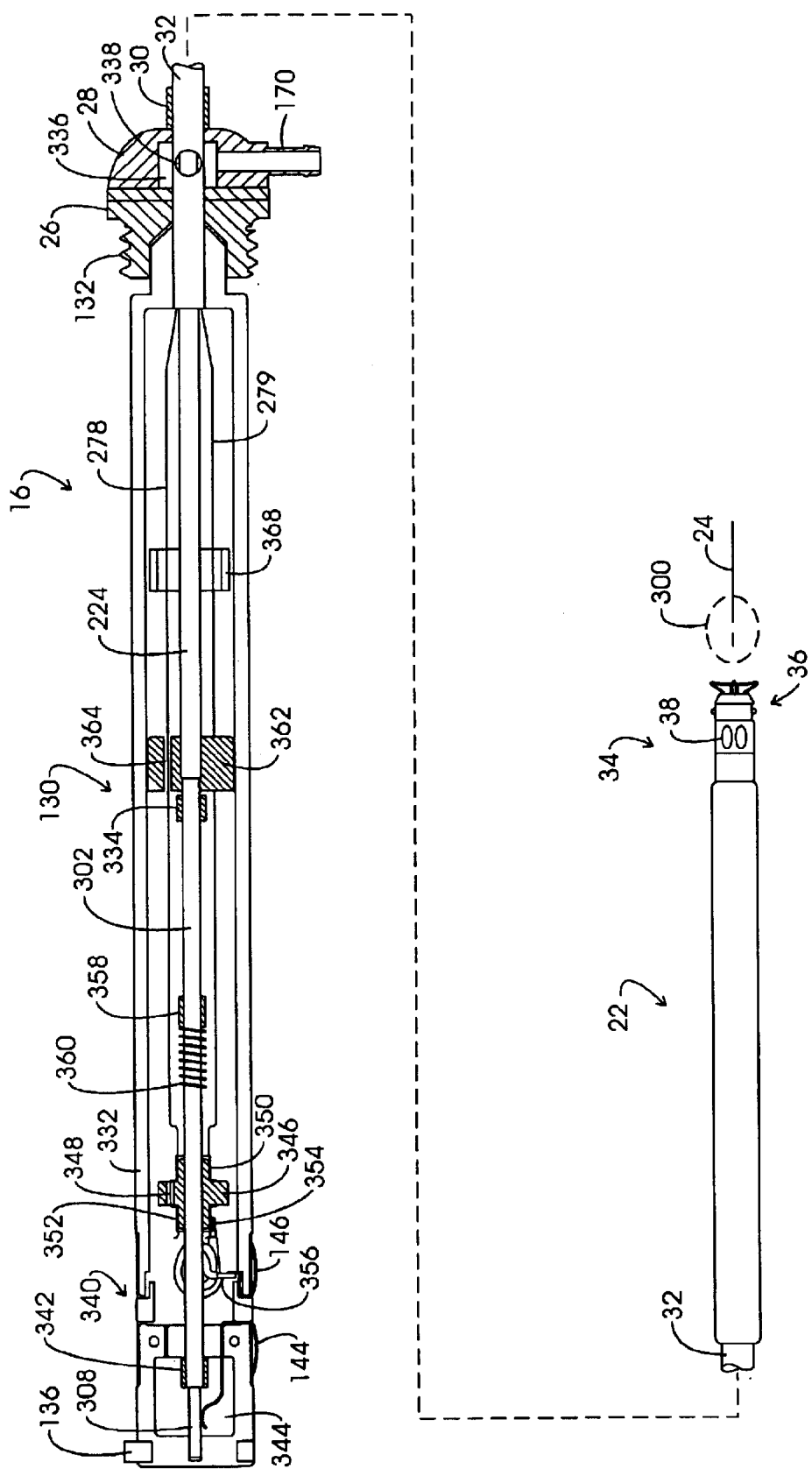
FIG. 11 is a partial sectional view of the disposable component of the instrument shown in FIG. 2 schematically showing the orientation of it's components prior to the deployment of a capture component.

FIGS. 11–13 provide partial sectional and exploded views of the disposable component 16 as it is positioned in confronting relationship with target tissue volume 300 at three stages in a specimen retrieval procedure. Looking to FIG. 11, the initial stage in the procedure is represented wherein tip 36 is in confronting relationship with the symbolic tumor or target tissue volume 300. Support housing 130 is formed from two identical moldings, one being shown at 332. These paired moldings are retained together adhesively as well as forwardly by connector 26 which, additionally, supports the cannula component 32. Component 32 extends through an evacuation chamber 336 formed within manifold 28. Vacuum communication with the chamber 336 is provided by a port or opening 338 in component 32.

Extending from adhesive attachment at a rearward bulkhead represented generally at 340 defined by the paired molding components, is the inward portion of the earlier-described support tube 302. Tube 302 additionally is anchored at the rearward side of bulkhead 340 by a plastic collar 342. Extending through the interior of the support tube 302 is the earlier-described precursor electrode tube 308, the rear tip of which extends along axis 24 into engagement with the paired molding components 332 and 334 at a cavity 344. That portion of the precursor electrode tube or rod 308 which extends rearwardly from support tube 302 is configured with an electrically conductive surface which receives electrical precursor electrode current through resiliently biased terminal component 144. The remainder of the precursor electrode tube 308, as it extends within support tube 302 is covered with electrically insulative shrink-wrap 310 (FIG. 8).

The five, nineteen-strand braided stainless steel cables 278–282 (FIG. 9) extend from their connection with the capture component 220 to a polymeric cable terminator component 346 which is slidably mounted over support tube 302 and moveable thereon in parallel with the instrument axis 24. Two of the braided pursing cables are stylistically represented in the drawing at 278 and 279. However, all five of these cables extend to and are connected with the cable terminator component 346. Component 346 is formed with five longitudinally disposed and radially spaced channels into each of which one of the cables 278–282 extend. In FIG. 11, cable 278 is seen extending through a channel 348. All five cables are retained or fixed to the terminator component 346 by two stainless steel collars. In this regard, a forward stainless steel collar or ferrule is shown at 350 while a rearward one is shown at 352. Collar or ferrule 352 additionally functions to apply electrosurgical cutting power or current simultaneously to all five of the pursing cables and, accordingly, it initially is nickel plated and then gold plated such that electrosurgical cutting current may be applied to it through a solder union 354. Union 354 connects the collar 352 with a braided multi-strand and highly flexible insulated copper cable 356. Cable 356, in turn, is soldered (or welded) to the forward electrical terminal assembly 146. Terminator component 346 is stabilized for slidable movement by two outwardly extending guidance tabs or ears, one of which has been described at 148 in conjunction with slot 152 in FIGS. 2 and 3. With this arrangement, as the five cables are electrically excited with electrosurgical cutting current, they are drawn in tension forwardly to, in turn, pull the terminator component 346 in slidable fashion forwardly over the support tube 302. This sliding movement under the drive of cable tension continues until the cable terminator component 346 encounters a cable stop 358 which is fixed to support tube 302 at a location which is selected to establish the maximum effective diametric extent of opening and overall length of the containment structure or cage generated by the capture component 220. This is the only adjustment required for developing a variation in such effective diametric extent and length dimensioning. For example, that effective diametric extent may range from about 10 mm to about 40 mm.

Note that as the component 346 approaches stop 358 it will engage a helical compression spring 360. Spring 360 functions to modulate the extent of tension applied to the cables such that the leaf tip regions as described in conjunction with FIGS. 6A–6C are more gradually vectored inwardly at the commencement of a pursing activity. This modulation of the tension on the cables is particularly beneficial where instrument 12 is utilized in conjunction with very dense tissue.

Drive imparted to capture component 220 is developed from drive tube 224 which, as described in connection with FIG. 3 is, in turn, driven from its outwardly disposed drive ears or tabs 160 and 162 which extend through slots, one of which is shown at 156 in FIG. 3. The drive member associated with these tabs is shown in FIG. 11 at 362 in its initial or home orientation. Drive member 362 is attached to drive tube 224 which is slidably mounted over support tube 302 and extends forwardly through the cannula component 32 into welded engagement with the pentagonal base portion 222 of capture component 220 (FIG. 4). As drive member 362 is driven forwardly, the five pursing cables 278–282 pass through it via five channels. One such channel is stylistically represented in the figure at 364 in conjunction with representative cable 278. Drive tube 224 as well as cables 278–282 additionally slide over a capture stop component 368 which is mounted to the housing 130 paired components. It is fixed in place in conjunction with earlier-described tab 172 (FIG. 2). The member 362 eventually will closely approach or engage the stop component 368 at the completion of pursing down with attendant derivation of a stall-induced spike at motor 186 (FIG. 3). A stop component 334 also is fixed to support tube 302 behind drive member 362. This component limits the return movement of member 362 during post fabrication testing.

As drive member 362 and cable driven terminator component 346 are driven forwardly to an extent wherein the capture component 220 reaches its maximum effective diametric extent, the components generally will assume the orientation shown in FIG. 12. Looking to that figure, note that spring 360 is now bottomed out, being fully compressed against stop member 358 by the terminator component 346. Further, drive member 362 has been moved forwardly toward capture stop 368. The figure also reveals in symbolic fashion that the capture component 220 has reached its maximum effective diametric extent. Further drive imparted to the drive member 362 will commence a more rapid pursing activity.

Studies have been carried out, for example, utilizing compressed porcine breast tissue which have determined that, where very dense tissue is encountered or where samples are taken from fibroadenomas, the earlier eyelet structures would from time-to-time fail by bending outwardly, a phenomena referred to as "fold-back". Generally the phenomena occurred as the capture component reached the orientation shown in FIG. 12. That fold-back phenomena has been corrected with a unique eyelet structuring including that described heretofore in connection with FIG. 6A-6C.

As the procedure progresses from the orientation of capture component 220, terminator component 346 and drive member 362 as shown in FIG. 12, forces are asserted on the cables as well as eyelet structure as the tip regions of the capture component 220 commence converging toward instrument axis 24. This continues until pursing is completed and motor stall is recognized. Looking to FIG. 13, the orientation of the components at this full pursing stage or capture position is shown. Note that terminator component 346 and compression spring 360 remain in engagement with cable stop 358 and that the drive component 362 is close or in engagement with capture stop 368. The leaf tip regions of the leafs of capture component 220 now have converged at instrument axis 24 to define a "basket" encapsulating the specimen 300. At this orientation, the dynamic frictional phenomena associated with the capturing activity is dormant and those portions of the cable forming a cutting surface are of minimum extent in view of full pursing.

Earlier leaf eyelet structures which, at times, in very dense tissue experienced fold-back phenomena were twisted into perpendicularity with respect to an associated leaf face through utilization of a neck structure. Referring to FIG. 14A, a tip region 370 of a leaf according to the earlier design is illustrated prior to the formational step of twisting its eyelet structure to perpendicularity with the leaf face. The leaf itself was constructed as described above having the same width and thickness and being formed of the same type 304 stainless steel. Note, as before, that the forward edge 372 is slanted inwardly. The eyelet structure is represented generally at 374 and is seen to have an outer width retaining a cable receiving aperture and a tie-off aperture extending between an interior eyelet edge 376 and an aligned outward eyelet edge 378 which is aligned with leaf edge 380. Note, however, that the structure 374 has a necked down region 382 formed to facilitate its twisting into perpendicularity. As before, the leaf tip region is symmetrically disposed about a leaf axis 384 and the chemically machined groove for receiving a guide tube is shown at 386 being symmetrically disposed about that axis leaf. The width of the neck region 380 is identified as, W, for the analysis to follow. Looking to FIG. 14B, leaf 372 is shown to have an eyelet structure length, L, and the eyelet structure 374 is now twisted into perpendicularity at neck region 382. FIG. 14C is a side view of the leaf showing it to have a thickness, T. It may be noted that, as compared with the embodiment of FIGS. 6A–6C, the larger diameter cable receiving aperture 388 is inboard of the smaller cable tie-off aperture 387.

The earlier leaf eyelet structure 374 was structurally analyzed along with the eyelet structure 2448 shown in FIG. 6A-6C. Referring to FIG. 15A, the fixed end geometry of a model for structurally analyzing the embodiments of FIGS. 6A–6C, and 14A–14C is presented. A fixed leaf face is represented at 390, while the eyelet structure extending perpendicular thereto is represented at 392 having a length, L, and being offset with respect to the leaf axis by an angle, φ. In the latter regard, a small initial bend due, for example, to assembly misalignment was assumed. As the leaf tip region advances into tissue, the leaf tip is assumed to be bent further through a range of angles, φ which was assumed to be 2.5° to 40°.

Looking additionally to FIG. 15B, a force diagram of the force analysis model is presented. The structural analysis determined the force required to elastically deflect an eyelet structure with respect to the noted range of angles φ. FIG. 15B shows the coordinate system assumed to be parallel and perpendicular to the bent tip so that the applied force, F, may be resolved into a bending and compressive force on the tip. The forces were computed with the assumption that the force is to be aligned with the mid-plane thickness of the three-mil thick leaf tip and additionally, the applied force is assumed to be applied in parallel with the leaf axis and aligned with the center-line of the cable receiving eyelet. In the diagram, it may be seen that the offset is identified as, C, while the force, F, included forces Fx along an assumed X-axis where Fx=F cos(φ) and Fy where Fy=F sin(φ). The force, F, was resolved into a bending and a compressive force upon the eyelet structure and the eyelet structure was assumed to be a beam of depth (thickness), T; width, W; and length, L, as above-described.

Assuming force, F, is aligned with the thickness or beam dimension of the eyelet structure, then compressive bending stress, Scb, a bending stress due to bending force acting perpendicular to the end of the eyelet structure may be expressed as follows:

$$Scb+M/Z=(L)Fy/(WT^2/6)=6(L)F \sin(\phi)/(WT^2) \tag{1}$$

where:
Scb=compressive bending stress, psi
M=L Fy=L F sin(φ), bending moment, in.lb
Z=W T²/6, section modulus, in.³
Direct Compressive Stress, Scd or Compressive stress due to direct force acting on the end of the eyelet structure parallel to the leaf axis, may be expressed as follows:

$$Scd=Fx/A=F \cos(\phi)/(WT) \tag{2}$$

where:
Scd=compressive direct stress uniformly distributed over cross section analyzed for stress, psi
A=WT, the cross sectional area of the neck region 382 in the case of FIGS. 14A–14C and the width, W, in FIGS. 6A–6C in square inches.

The directions of the compressive bending and direct stresses are parallel. Therefore these stresses are additive and their sum, Sc, may be expressed as follows:

$$Sc=Scd+Scb=F \cos(\phi)/(WT)+6(L)F \sin(\phi)/(WT^2)=Sy \text{ psi} \tag{3}$$

Compressive stress, Sc, is set equal to the yield stress, Sy, to obtain the maximum force, F, that the eyelet structure can withstand before yielding. Solving equation (3) for, F, results in the following expression:

$$F=(WT^2Sy)/[T \cos(\phi)+6L \sin(\phi)] \tag{4}$$

The above expressions are established for an offset value, C, of zero. This offset provides an additional moment on the end of the beam causing the eyelet structure to bend. Accordingly, the bending stress equation now may be as follows:

$$Scb=(Mo+M)/Z=[CF \cos(\phi)+(L)Fy/(WT^2/6)]=6(L)F \sin(\phi)$$

where:
Mo=C F cos(φ)=moment on the end of the eyelet structure (in. lb.) due to the force offset
C=force offset distance from center line of eyelet structure, in.
The resulting force equation with the offset, C, may be expressed as follows:

$$F=(WT^2Sy)/\{T \cos(\phi)+6[C \cos(\phi)+L \sin(\phi)]\} \tag{6}$$

Looking at Table 1, the computed force, F, in pounds required to elastically deflect the eyelet structures represented in FIGS. 14A–14C and FIGS. 6A–6C are set forth. Note, that for an offset value, C, of zero, the strength performance values of the eyelet structure of FIGS. 6A–6C are almost twice those of FIG. 14A-14C. Correspondingly, for an offset, C, value of 0.15 inch for the structure of FIG. 14A-14C as compared with an offset, C, value in inches of 0.010 inch for the structure of FIG. 6A-6C again shows an improvement amounting to almost twice the eyelet structural capacity.

Figure 16A:
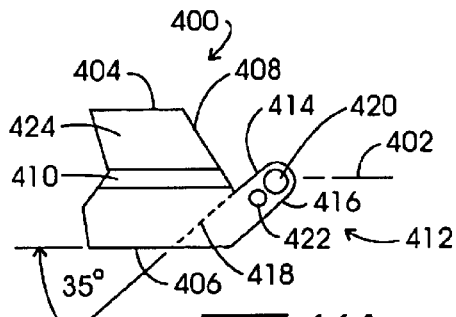
FIG. 16A is a plan view of the tip region of a capture component leaf showing another eyelet structure at a stage in formation.

Referring to FIG. 16A another embodiment of a leaf tip region is shown identified generally at 400. The region 400 is illustrated as it appears during a stage of formation wherein the eyelet structure has not been moved into perpendicularity with the faces of the associated leaf. That leaf is seen to extend along a leaf axis 402 between leaf side edges 404 and 406 to a forward edge 408. A centrally disposed chemically milled groove 410 is provided to support the earlier-described cable guide channel which can be provided as a polyamide tube which extends to a guide outlet adjacent the edge 408. The eyelet structure for this embodiment, represented generally at 412, is shown having an eyelet width defined between oppositely disposed eyelet edges 414 and 416. Interior eyelet edge 414 is at an acute angle of 35° with respect to and diagonally toward the leaf axis 402. The figure further shows a dashed bend line 418, which is aligned with the interior eyelet edge 414, and extends within the tip region 400 to leaf side edge 406. A cable-receiving aperture is shown at 420 and inwardly disposed therefrom is a tie-off aperture 422.

Figure 16B:
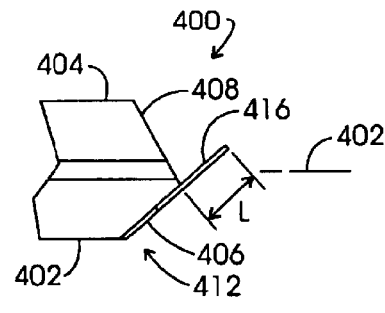
FIG. 16B is a plan view of the tip region of FIG. 8A showing its eyelet structure bent into perpendicularity with respect to a leaf face.
Figure 16C:
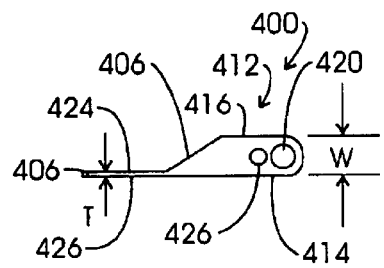
FIG. 16C is a side view of the tip region of FIG. 16B.

FIGS. 16B and 16C illustrate the tip region 400 following the bending of eyelet structure 412 into perpendicularity with the oppositely disposed faces 424 and 426 of the leaf structure. Note that the eyelet structure 412 is of substantially constant width, its length for computational purposes being shown as, L, in FIG. 16B and its width, W, and thickness, T, being identified in FIG. 16C. With the arrangement shown, the 35° acute angle will locate the cable-receiving eyelet 420 forwardly of a guide outlet mounted within groove 14 and about the leaf axis 402. This facilitates the play-out of cable from that guide outlet and through the cable-receiving aperture 420.

Figure 17A:
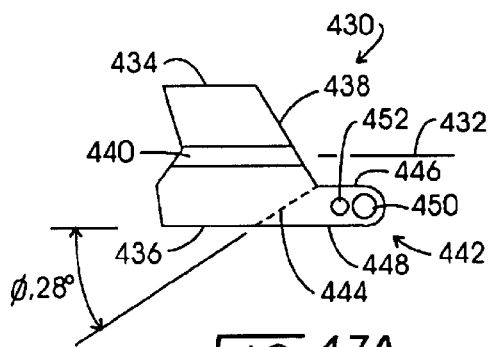
FIG. 17A is a plan view of a tip region of a capture component leaf showing another eyelet structure at a stage in its formation.

Referring to FIG. 17A, another embodiment for a leaf tip region and associated eyelet structure is presented. The tip region is represented in general at 430 as extending along a leaf axis 432 between leaf sides 434 and 436 to a forward edge 438. As before, a groove 440 is chemically milled in the leaf which is symmetrically disposed about leaf axis 432 and functions to support a cable guide channel having an outlet adjacent edge 438. An eyelet structure is represented in general at 442 in an orientation prior to its being bent or folded into perpendicular orientation with respect to the faces of the leaf. Bend line 444 is canted at an acute angle of 28° with respect to leaf axis 432. Eyelet structure 442 is configured with oppositely disposed eyelet edges 446 and 448 to establish a constant eyelet width. Note that eyelet edge 448 is configured as an extension of coextensive leaf edge 436. Structure 442 is configured having an outboard cable receiving aperture 450 as well as an inboard tie-off aperture 452. Looking additionally to FIGS. 17B and 17C, the eyelet structure 442 is seen oriented perpendicularly to the faces of the leaf structure, the eyelet structure length, L, being identified in FIG. 17B and its width, W, and thickness, T, being identified in FIG. 17C. Note in the latter figure that the eyelet extends upwardly from the plane of the faces of the involved leaf at an acute angle γ of 28°.

Figure 18A:
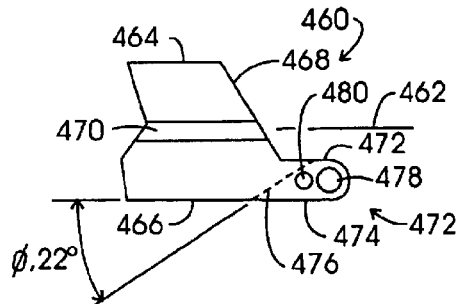
FIG. 18A is a plan view of the tip region of a capture component leaf showing another eyelet structure at a stage in it's formation.
Figure 18B:
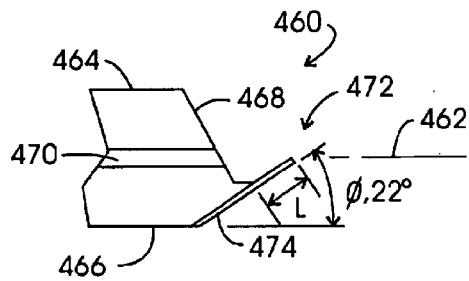
FIG. 18B is a plan view of the tip region of FIG. 18A showing the eyelet structure bent into perpendicularity with respect to the face of the leaf.
Figure 18C:
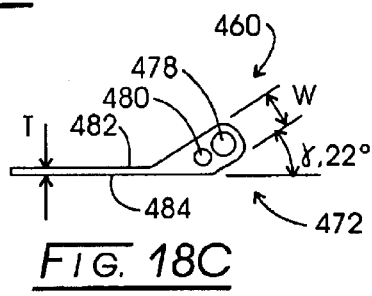
FIG. 18C is a side view of the tip region of FIG. 18B.

Referring to FIG. 18A, another eyelet structure is revealed in conjunction with leaf tip region 460. The region 460 includes leaf sides 464 and 466 which extend symmetrically about leaf axis 462 and forwardly to a leaf forward edge 468. A groove 470 is chemically milled in one face of the leaf which is symmetrically disposed about leaf axis 462. For the present embodiment, an eyelet structure is represented generally at 472 having oppositely disposed eyelet edges 472 and 474. The figure shows the eyelet prior to its being bent about a dashed bend line 476 into a perpendicular orientation. Bend line 476 is canted at an acute angle, φ of 22°. Structure 472 includes an outwardly disposed cable receiving aperture 478 and an inwardly disposed tie-off aperture 480. In contrast to FIG. 17A wherein bend line 444 extends from forward edge 438 to leaf side 436, bend line 476 in FIG. 18A is seen to extend from a position upon eyelet edge 472 to leaf edge 466 which is coextensive with an aligned eyelet edge 474. Referring additionally to FIGS. 18B and 18C, the forward region 460 is shown with the eyelet structure 472 having been bent upwardly to a perpendicular orientation with respect to the faces 482 and 484 of the leaf. Those faces are seen in FIG. 18C in conjunction of an identification of thickness, T. The figure also identifies the constant width, W, of the structure 472. Note in the figure that the structure 472 is canted upwardly with respect to the leaf faces at an acute angle, γ of 22°. FIG. 18B identifies the length, L, of the eyelet structure.

Figure 19A:
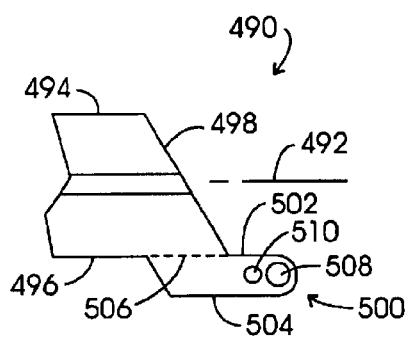
FIG. 19A is a plan view of the tip region of a capture component leaf showing another eyelet structure at a stage in it's formation.

Referring to FIG. 19A, another eyelet structure is portrayed in conjunction with leaf tip region 490. Region 490 is shown with leaf axis 492 which is centrally disposed between leaf sides 494 and 496 which extend in parallel with leaf axis 492 to forward edge 498. The eyelet structure, integrally formed with tip region 490, is represented generally at 500 and is seen to be formed with oppositely disposed parallel eyelet edges 502 and 504. Eyelet structure 500 is shown at a stage in its formation prior to its being bent outwardly into perpendicularity with the faces of the leaf about a bend line shown in dashed form at 506. The interiorly disposed eyelet edge 502 is aligned with coextensive leaf edge 496 and incorporates an outwardly disposed cable-receiving aperture 508 and a tie-off aperture 510. Looking to FIG. 19B, structure 500 is shown in its orientation following bending to perpendicularity with respect to a leaf face. The figure also identifies the eyelet structure length, L. FIG. 19C illustrates the leaf and eyelet structure thickness, T, as it extends between leaf faces 512 and 514. Also identified in the figure is the eyelet structure width, W. It may be observed that interiorly disposed aligned eyelet edge 502 is coplanar with leaf face 512 and that the width, W, is constant. For all of the leaf tip region versions above-described, the leafs are formed of a type 304 stainless steel, full hard, having a width of 0.080 inch and a thickness of 0.003 inch.

Turning to FIGS. 20A and 20C, a force analysis model is presented for determining the amount of force required to elastically deform eyelet structure 412 described in conjunction with FIGS. 16A–6C. In FIG. 20A the geometry at hand seen to be is one where a force, F, is applied to the outward region of structure 412 and deforming force is computed with respect to a sequence of bend angles, φ. Force, F, is applied parallel with the leaf axis to cause two-dimensional force and stress components. Computation is seen to be carried out with a fixed end geometry 516 as seen in FIG. 20B. Looking to FIG. 20C, a force diagram is revealed showing the force, F, its components Fy being equal to F sin(φ) and Fx being equal to F cos(φ).

Compressive stress $Sc_1$ in a vertical plane caused by horizontal forces in pounds per square inch may be expressed as follows:

$$Sc_1 = Scd + Scb = F\cos(\varphi)/(W\,T) + 6(L)F\sin(\varphi)(W\,T^2) \quad (7)$$

$$= WTF\cos(\varphi)/(W^2T^2) + 6W(L)F\sin(\varphi)/(W^2T^2)$$

Bending moment, Mo in the vertical width of the eyelet structure caused by force, F, a distance, C, above the face of the leaf is the product, CF. Accordingly, the compressive bending stress across the thickness of the eyelet structure may be expressed as follows:

$$Sc_2 = Mo/Z_2 = 6CF/(TW^2) = 6CTF/(W^2T^2) \quad (8)$$

Maximum combined compressive stress, Sc in pounds per square inch representing stress acting in two perpendicular planes may be expressed as follows:

$$Sc=(Sc_1+Sc_2)/2+/-\sqrt{[(Sc_1-Sc_2)/2]^2+S^2_{xy}} \quad (9)$$

Of the expressions (7) and (8) above, the compressive bending stress, $Sc_1$ of expression (7) is determined to be the greater of the two stresses over a range of deflection angles. Therefore this stress is used to calculate maximum force, F, that the eyelet structure can withstand in accordance with the following expressions:

$$Sc_1=F\cos(\phi)/(WT)+6(L)F\sin(\phi)/(WT^2)=Sy \quad (10)$$

$$F=(WT^2Sy)/\{T\cos(\phi)+6L\sin(\phi)\} \quad (11)$$

The forces required to elastically deflect the eyelet structure 412 of FIGS. 16A–16C are compiled with respect to angles of deflection, φ in Table 2. In the compilation, C, is shown as zero inasmuch as it pertains to stress in a perpendicular direction to the direction of stress being calculated.

Figure 17B:
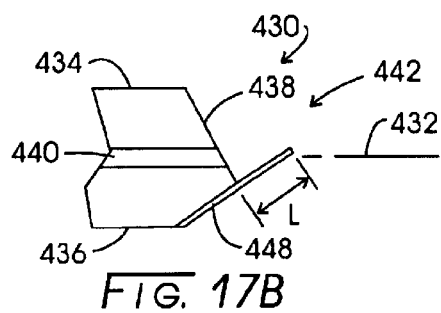
FIG. 17B is a plan view of the tip region of FIG. 17A showing the eyelet structure bent into perpendicularity with respect to a leaf face.
Figure 17C:
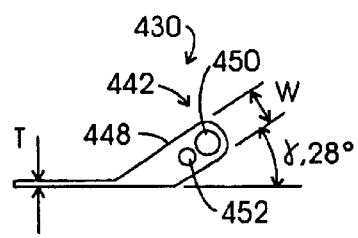
FIG. 17C is a side view of the tip region of FIG. 17B.

Now turning to FIGS. 21A–21C a force analysis model is provided for the eyelet structure represented at FIGS. 17A–17C and one component for the eyelet structure represented in conjunction with FIGS. 18A–18C. In FIG. 21A, X and Y coordinates are identified in conjunction with a force arrow which is parallel with the leaf axis and applied to the outer portion of the eyelet structure. Additional force application geometry is represented in FIG. 21B. The force diagram of FIG. 21C identifies these force factors with respect to angle φ, an arrangement wherein Fx=F cos(φ) and Fy=F sin(φ).

Force, F, for the embodiment of FIGS. 17A–17C is calculated in a manner similar to expression (11) above as follows:

$$F=(WT^2Sy)/\{T\cos(28)\cos(\phi)+6L\sin(\phi)\} \quad (12)$$

The resultant force values for the FIGS. 17A–17C embodiment is compiled in Table 2 in conjunction with a sequence of bend angles.

Compressive bending stress, $Sc_1$ for the embodiment of FIGS. 18A–18C may be calculated as follows:

$$F=Sy/[\cos(\phi)/A+FL\sin(\phi)/Z_1] \quad (13)$$

where:

A is cross sectional area of angle and $Z_1$ is section modulus.

Figure 22A:
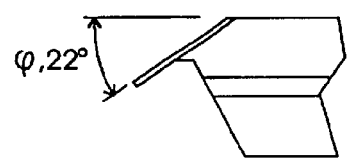
FIGS. 22A–22C combine to provide a force analysis model with respect to the eyelet structure of FIGS. 18, FIG. 22A and 22B representing geometric aspects and FIG. 22C being a force diagram.
Figure 22C:
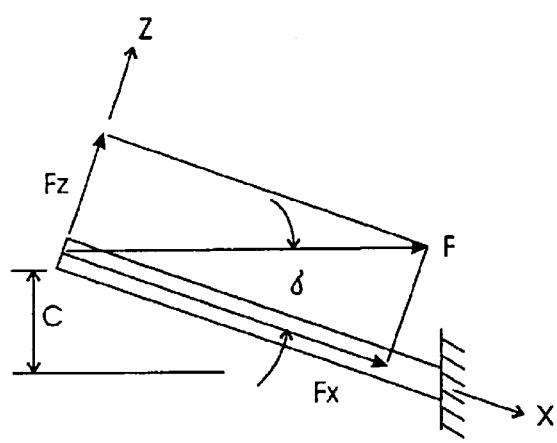
Figure 22B:
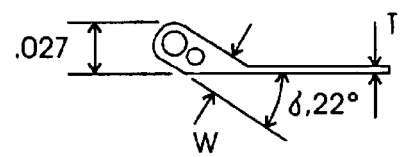

Looking to the force analysis model represented in FIGS. 22A–22C it may be observed that the force, F, geometry and force diagram look to an offset, C, in conjunction with x and z components such that Fx=F cos(γ) and Fz=F sin(γ).

For this model, the following expression is employed to compute force, F:

$$F=Sy/[C\cos(\gamma)/Z_2] \quad (14)$$

where:

$Z_2$ is a section modulus.

Figure 19B:
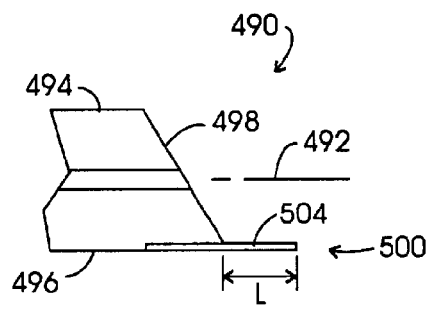
FIG. 19B is a plan view of the tip region of FIG. 19A showing the eyelet structure bent into perpendicularity with respect to a leaf face.
Figure 19C:
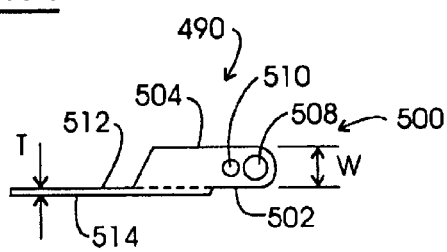
FIG. 19C is a side view of the tip region of FIG. 19B.

The eyelet structure geometry for the embodiment of FIGS. 19A–19C is similar to the geometry of the embodiment of FIGS. 6A–6C. Because of the similarity of dimensions, the force values tabulated for, C=0 in Table 1 are appropriate for this embodiment. Where the force is offset such that, C=0.013 inch, then the following expression applies:

$$F=(W*T*T*Sy)/\{T*COS(\phi)+6*[C*COS(\phi)+L*SIN(\phi)]\} \quad (15)$$

While the above-described eyelet structure stabilization designs eliminated fold-back phenomena, capture component investigation determined that, from time-to-time, particularly in connection with dense tissue, one or more of the cables 278–282 would break under tensional load. Revisiting FIG. 13, this investigation revealed that breakage occurred at full purse-down of the five eyelet structures converging at instrument axis 24. As this full pursing geometry is reached as schematically represented in FIG. 13, motor 186 (FIG. 3) will enter a stall condition and the control assembly 70 (FIG. 1) will respond to the generation of about a 130 milliamp spike or current excursion at the motor to terminate application of electrosurgical cutting energy to the pursed cutting cables. Returning to FIG. 10, essentially the only arc-carrying component of the cables at this point in the procedure just prior to controlled cutting arc shutdown will be a "bare" length between the guide outlet of the polyamide guide tube and the cable receiving aperture of an eyelet structure in addition to the short length extending to the cable knot at the tie-off aperature of an adjacent leaf. One such bare length is identified at 520 in the figure extending from the guide outlet of guide tube 272 to eyelet structure 244e. Cable breakage, for the most part, occurred at such locations. At this point in operational time there is no cable movement such that there is no frictional loss component and the cables then are called upon to endure all of the driving force deliverable by motor 186.

Figure 23:
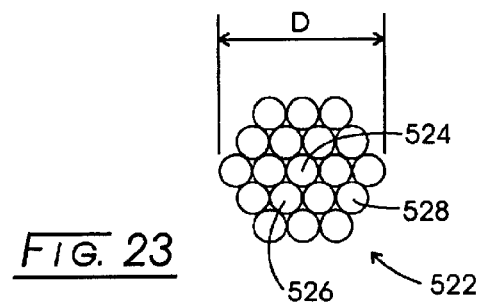
FIG. 23 is a sectional representation of a capture component cable employed with the apparatus of the invention.

The cables which have been employed with the capture components have had a nineteen strand configuration formed from a type 304 stainless steel. These strands have a quite small diameter of about 1.2 mils to the extent that observing them calls for magnification. Referring to FIG. 23, the cross section of a nineteen strand cable is depicted. Note that it is configured having a center strand 524. That center strand 524 is surrounded by a grouping of six strands represented at 526. Grouping 526 in turn, is surrounded by an outer twelve strand group represented at 528. With the arrangement, the cable diameter, D, will represent a linear array of five adjacent strands or nominally six mils. That nominal diameter achieves necessary deployment characteristic permitting play-through through the cable receiving apertures. However, the cables are called upon to sustain imposed tensile stresses in the environment of an RF cutting arc which appears to be within a range of about 1400° F. to about 1600° F. based on the observed strength reduction in the cables.

Studies were carried out with respect to six mil diameter, 6.94 mil diameter and 8 mil diameter nineteen strand cables formed with a type 304 stainless steel. Additionally, these studies were carried out with respect to a nineteen strand cable structure having an 8 mil nominal diameter and the noted 6.94 mil diameter formed of a type 316 stainless steel. Strength tests were carried out both under room temperature conditions and in the simulated temperature environment of an electrosurgical cutting arc.

Figure 24:
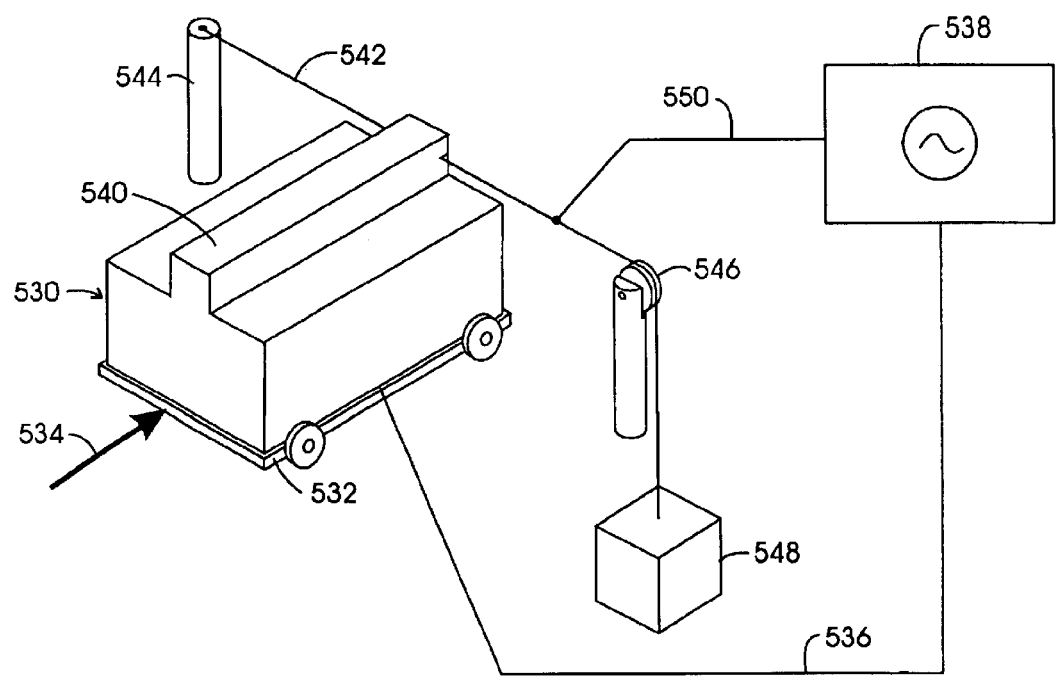
FIG. 24 is a schematic diagram of a test carried out to evaluate pursing cable components of the apparatus of the invention.

Referring to FIG. 24, a test setup for these studies for carrying out load testing under electrosurgical cutting conditions is revealed. The figure shows a block of breast phantom represented generally at 530. Breast phantom 530 was prepared by Pharmaceutical Innovations, Inc. of Newark, N.J. to duplicate the electrical properties and arc cutting characteristics of dense human breast tissue, Such dense tissue exhibits lower electrical resistivity and therefore results in a more intense, higher current electrosurgical cutting arc. In the tabulations to follow, this high temperature environment is referred to as "RF power applied". Phantom 530 rests upon a return electrode pad (not shown)

which, in turn, rests upon a wheeled cart 532 which was driven over a horizontal smooth surface at a rate of 3 mm/second as represented by the arrow 534. That rate of movement is the advancement rate for capture component 220 as imparted to the drive tube 224 from yoke 210 (FIGS. 3 and 4). The return electrode pad was coupled in conventional fashion as represented at line 536 with the return input of an electrosurgical generator 538. Generator 538 was provided as a model 3000 RF Controller, marketed by Neothermia Corp. (supra). Note that phantom breast block 530 was configured at its upper region to provide an upwardly protruding elongate block 540 having a widthwise extent of 3 cm. Four foot lengths of cable were tested, one being represented at 542. One end of test cable 542 was fixed to a support as at 544 and then extended in horizontal fashion across a supported pulley 546, whereupon the opposite or free end of the cable was attached to a weight pan represented by block 548. Electrosurgical cutting energy was applied to the test cable 542 in adjacency with the block 540 as represented at line 550. Accordingly, during the movement of cart 532 with an application of FF electrosurgical cutting energy to the test cable 542, the applied load at pan 548 was increased in 100 gram increments until breaking load was reached. The procedure also decreased the load in 50 gram increments to identify loads which cable can sustain.

The results of the test involving the setup of FIG. 24 as well as room temperature tests and computations are set forth in Table 3. Referring to Table 3 note, initially, that the earlier-utilized cable having a nominal six mil diameter and formed of A type 304 stainless steel exhibited a load strength of 7.53 pounds at room temperature. However, when RF power was applied as described in connection with FIG. 24 the minimum load at which cable break occurred was 1.03 pounds. This nominally one pound minimum load at cutting temperatures can evoke cable breakage.

Where cable formed of a type 304 stainless steel is increased in diameter to 8.2 mils, then the minimum load at which cable breaks advances to 12.12 pounds and that same minimum load where RF power is applied advances to 2.69 pounds, a strength which is acceptable.

Next in the tabulation is the utilization of the larger diameter 8 mil cable formed of a type 316 stainless steel. Note that the minimum load under room temperature conditions at which cable breaks advances slightly to 12.47 pounds and that minimum load at which cable breaks at a cutting arc environment (RF power applied) advances importantly to 3.57 pounds, again a value which is acceptable.

Calculations then were made for a cable formed with a type 316 stainless steel having a strand diameter of 1.388 mils and an overall nominal cable diameter of 6.94 mils, i.e., about 7 mils. The case A calculations employed the following input values:

(1) Breaking strength of stainless steel 316 cable at room temperature, (2) Weight of a known length of cable which is used to accurately calculate total cross-sectional area of multi-strand cable, and (3) The ratio of breaking load under RF power conditions to breaking load at room temperature. Those ratios are located in the far rightward column of Table 3. Note that the computed minimum load at which cable breaks for case A advanced to 9.38 pounds, while the calculated minimum load at which cable breaks under high temperature RF power applied conditions is an acceptable 2.68 pounds.

Case B calculations were based upon all three of the above factors and predicts a value that is 5.7% higher than actual.

The Case C calculations were based upon the utilization of a type 304 stainless steel with the noted 6.94 mil cable diameter and resulted in a computation of a minimum load at which cable breaks for room temperature is being 10.03 pounds and a minimum load at which cable breaks at electrosurgical arc temperatures of 1.37 pounds.

The fourth level of Table 3 sets forth data obtained with actual cable having a strand diameter of 1.388 mils and an overall cable diameter of 6.94 mils. Formed of a type 316 stainless steel, the minimum load at which cable breaks at room temperature was found to be 10.34 pounds and the minimum load at which cable breaks for the high temperature case where RF power is applied is 2.80 pounds a highly desirable value. The approximately 7 mil overall cable diameter was found to be acceptable for necessary mechanical deployment characteristics such as pass-through and the like, while, in comparison the 8 mil nominal diameter cable was marginally acceptable from that standpoint. Thus, the system performs in conjunction with cable having a nominal diameter of between about 6 mils and about 8 mils.

Comparing the 2.80 pounds minimum load at which cable breaks for the type 316 stainless steel data with the type 304 stainless steel data corrected for the larger strand size as set forth in case C shows, that the cable formed with a type 316 stainless steel is more than 104% stronger (a factor of 2.04) than corresponding cable formed with a type 304 material. Published data concerning elevated temperature tensile strength of a type 316 stainless steel and a corresponding type 304 stainless steel indicates that the type 316 material should only exhibit about 30% greater strength at the elevated temperatures associated with electrosurgical cutting. In general the cable strands will each have a diameter of about 1.0 mils to about 1.6 mils.

Type 316 stainless steel has the following formulation: 0.08 weight percent carbon—maximum, 2.00 weight percent manganese—maximum, 0.045 weight percent phosphorus—maximum, 0.030 weight percent sulfur—maximum, 1.00 weight percent silicon—maximum, 16 to 18 weight percent chromium, 10 to 14 weight percent nickel, and 2 to 3 weight percent molybdenum.

Type 316 L stainless steel has the following formulation: 0.03 weight percent carbon—maximum, 2.00 weight percent manganese—maximum, 0.045 weight percent phosphorus—maximum, 0.030 weight percent sulfur—maximum, 1.00 weight percent silicon—maximum, 16 to 18 weight percent chromium, 10 to 14 weight percent nickel, and 2 to 3 weight percent molybdenum.

Type 316 stainless steel has 2% to 3% molybdenum by weight as contrasted with A type 304 stainless steel which has 0.6% maximum. Type 316 stainless steel has slightly more nickel (10–14%) by weight and slightly more chromium (16–18%) by weight than a type 304. The result is that the type 316 steel is substantially more resistant to corrosion/oxidation. Type 316L stainless steel has a slightly lower carbon content (0.03% max. as opposed to 0.08% max. by weight). When used herein, a type 316 stainless steel is intended to mean each of the varieties.

Other metals or alloys which may be employed in fashioning the capture cables offering high strength and good corrosion/oxidation resistance at elevated temperatures include the following:

(a) Nickel based alloys, e.g., Hastelloy Alloy C, having the following formulation: 0.08 to 0.12 weight percent carbon—1.0 weight percent Manganese—1.0 weight percent silicon—4.0 to 7.0 weight present tungsten—3.0 to 5.25 weight percent molybdenum—15 to 18 weight percent chromium—2.5 weight percent cobalt—0.2 to 0.4 weight percent vanadium—0.04 weight percent phosphorous—0.03 weight percent sulfur—balance, nickel; Rene-41 having the following formulation: 18.0 to 20.0 weight percent chromium—10.0 to 12.0 (max) weight percent cobalt—9.0 to 10.5 weight percent carbon—0.5 weight percent silicon—0.1 weight percent manganese—3.0 to 3.3 weight percent titanium—1.4 to 1.6 weight percent aluminum—balance, nickel; Inconel 718 having the following formation: 0.08 weight percent carbon—0.35 weight percent manganese 50 to 55 weight percent nickel—17 to 21 weight percent chromium—4.75 to 5.5 weight percent cobalt and tantalum—2.8 to 3.3 weight percent molybdenum—1.0 weight percent cobalt—0.65 to 1.5 weight percent titanium—0.2 to 0.8 weight percent aluminum—0.35 weight percent silicon—0.3 weight percent copper—0.015 weight percent phosphorous—0.006 weight percent boron—balance, iron.

(b) Martensitic Stainless Steels, e.g. Type 414 having the following formulation: 0.15 (max) weight percent carbon—11.5 to 13.5 weight percent chromium—1.25 to 2.5 weight percent nickel—1.00 (max) weight percent manganese—1.0 (max) weight percent silicon—0.040 (max) weight percent phosphorous—0.030 (max) sulfur; Type 431 having the following formulation: 0.20 (max) weight percent carbon—15 to 17 weight percent chromium—1.25 to 2.50 weight percent nickel—1.00 (max) weight percent manganese—0.040 (max) weight percent phosphorous—0.030 (max) weight percent sulfur—1.00 (max) weight percent silicon—balance, iron.

(c) Tungsten and Tungsten-based Alloys, e.g., tungsten/26 weight percent aluminum.

Since certain changes may be made to the above apparatus without departing from the scope of the invention herein involved, it is intended that all matter contained in the above description or shown in the accompanying drawings shall be interpreted as illustrative and not in a limiting sense.

TABLE 1

Force, F, (lbs) Required To Elastically Deflect Eyelet Structure

| | Eyelet Structure FIGS. 14 | | Eyelet Structure FIGS. 6 | |
|---|---|---|---|---|
| W | 0.020 in | 0.020 in | 0.023 in | 0.023 in |
| L | 0.082 in | 0.082 in | 0.046 in | 0.046 in |
| T | 0.003 in | 0.003 in | 0.003 in | 0.003 in |
| Sy | 150000 psi | 150,000 psi | 150,000 psi | 150,000 psi |
| C | 0 in | 0.015 in | 0 in | 0.010 in |
| φ | F | F | F | F |
| 2.5 | 1.104 | 0.236 | 2.065 | 0.414 |
| 5.0 | 0.589 | 0.199 | 1.148 | 0.358 |
| 7.5 | 0.402 | 0.173 | 0.796 | 0.315 |
| 10.0 | 0.305 | 0.153 | 0.610 | 0.282 |
| 12.5 | 0.247 | 0.137 | 0.495 | 0.256 |
| 15.0 | 0.207 | 0.124 | 0.418 | 0.235 |
| 17.5 | 0.179 | 0.114 | 0.362 | 0.217 |
| 20.0 | 0.158 | 0.106 | 0.319 | 0.202 |
| 22.5 | 0.141 | 0.098 | 0.286 | 0.190 |
| 25.0 | 0.128 | 0.092 | 0.260 | 0.179 |
| 27.5 | 0.117 | 0.087 | 0.239 | 0.169 |
| 30.0 | 0.109 | 0.083 | 0.221 | 0.161 |
| 32.5 | 0.101 | 0.079 | 0.206 | 0.154 |
| 35.0 | 0.095 | 0.075 | 0.193 | 0.148 |
| 37.5 | 0.089 | 0.072 | 0.182 | 0.142 |
| 40.0 | 0.085 | 0.070 | 0.173 | 0.138 |

TABLE 2

Force, F, (lbs) Required To Elastically Deflect

| | Eyelet Structure FIGS. 16 | | Eyelet Structure FIGS. 17 | | Eyelet Structure FIGS. 18 | | | | Eyelet Structure FIGS. 19 | |
|---|---|---|---|---|---|---|---|---|---|---|
| W | 0.023 in | | 0.023 in | | 0.023 in | 0.023 in | 0.023 in | | 0.023 in | |
| L | 0.037 in | | 0.046 in | | 0.046 in | 0.046 in | 0.046 in | | 0.046 in | |
| T | 0.003 in | | 0.003 in | | 0.003 in | 0.003 in | 0.003 in | | 0.003 in | |
| Sy | 150,000 psi | | 150,000 psi | | 150,000 psi | 150,000 psi | 150,000 psi | | 150,000 psi | |
| C | 0 in | | 0 in | | 0 in | 0.016 in | 0.006 in | | 0.013 in | |
| φ | F | φ | F | φ | F | F | F | φ | F |
| 15.0 | 0.514 | 10.0 | 0.614 | 2.5 | 5.065 | 1.409 | 3.758 | 2.5 | 0.334 |
| 17.5 | 0.446 | 12.5 | 0.498 | 5.0 | 3.496 | 1.413 | 3.768 | 5.0 | 0.296 |
| 20.0 | 0.394 | 15.0 | 0.420 | 7.5 | 2.673 | 1.420 | 3.786 | 7.5 | 0.267 |
| 22.5 | 0.354 | 17.5 | 0.363 | 10.0 | 2.167 | 1.429 | 3.812 | 10.0 | 0.243 |
| 25.0 | 0.322 | 20.0 | 0.320 | 12.5 | 1.825 | 1.442 | 3.845 | 12.5 | 0.224 |
| 27.5 | 0.295 | 22.5 | 0.287 | 15.0 | 1.579 | 1.457 | 3.886 | 15.0 | 0.207 |
| 30.0 | 0.273 | 25.0 | 0.261 | 17.5 | 1.394 | 1.476 | 3.936 | 17.5 | 0.194 |
| 32.5 | 0.255 | 27.5 | 0.239 | 20.0 | 1.249 | 1.498 | 3.995 | 20.0 | 0.182 |
| 35.0 | 0.239 | 30.0 | 0.221 | 22.5 | 1.134 | 1.524 | 4.063 | 22.5 | 0.172 |
| 37.5 | 0.226 | 32.5 | 0.206 | 25.0 | 1.040 | 1.553 | 4.142 | 25.0 | 0.163 |
| 40.0 | 0.214 | 35.0 | 0.193 | 27.5 | 0.962 | 1.587 | 4.232 | 27.5 | 0.156 |
| 42.5 | 0.204 | 37.5 | 0.183 | 30.0 | 0.897 | 1.626 | 4.335 | 30.0 | 0.149 |
| 45.0 | 0.195 | 40.0 | 0.173 | 32.5 | 0.841 | 1.669 | 4.451 | 32.5 | 0.143 |
| 47.5 | 0.187 | 42.5 | 0.165 | 35.0 | 0.794 | 1.719 | 4.583 | 35.0 | 0.138 |
| 50.0 | 0.181 | 45.0 | 0.158 | 37.5 | 0.752 | 1.774 | 4.732 | 37.5 | 0.134 |
| 52.5 | 0.174 | 47.5 | 0.151 | 40.0 | 0.716 | 1.838 | 4.900 | 40.0 | 0.130 |

TABLE 3

Comparison of Breaking Strength of SS304 and SS316 Cables at Room Temperature and Under RF Power Application Conditions

| Wire Material | Cable Diameter Based on 5X Strand Diameter (inch) | Test Conditions | Cross-Sectional Area of 19 Strands of Cable (sq. inch) | Cable Strand Diameter (19 strands/cable) (inch) | Maximum Load at Which Cable Breaks (pounds) | Tensile Strength of Cable (pounds/sq. inch) | Ratio of RF Powered to R.T. Breaking Strength |
|---|---|---|---|---|---|---|---|
| SS304 | 0.0060 | Room Temperature | 0.0000216 | 0.00120 | 7.53 | 349,193 | |
| | | RF Power Applied | 0.0000216 | 0.00120 | 1.03 | 47,765 | 0.1368 |
| SS304 | 0.0082 | Room Temperature | 0.0000402 | 0.00164 | 12.12 | 301,680 | |
| | | RF Power Applied | 0.0000402 | 0.00164 | 2.69 | 66,957 | 0.2219 |
| SS316L | 0.0080 | Room Temperature | 0.0000382 | 0.00160 | 12.47 | 326,440 | |
| | | RF Power Applied | 0.0000382 | 0.00160 | 3.57 | 93,455 | 0.2863 |
| SS316 | 0.00694 | Room Temperature | 0.000028729 | 0.001388 | 10.34 | 359,915 | |
| | | RF Power Applied | 0.000028729 | 0.001388 | 2.80 | 97,463 | 0.2708 |
| | | Case A-Calculations Based on RF/R.T. Ratio For 0.008" O.D SS316L Cable Tested and Tensile Strength of 326 KSI for 8 Mil Cable | | | | | |
| SS316L | 0.00694 | Room Temperature | 0.000028729 | 0.001388 [assumed] | 9.38 | 326,440 [assumed] | |
| | | RF Power Applied | 0.000028729 | 0.001388 [assumed] | 2.68 (4.3% lower than actual value of 2.8 lbs.) | 93,455 | 0.2863 [assumed] |
| | | Case B-Calculations Based on RF/R.T. Ratio fo 0.008" O.D. SS316L Cable Tested and Actual Tensile Strength of 360 KSI for New Cable | | | | | |
| SS316 | 0.00694 | Room Temperature | 0.000028729 | 0.001388 [assumed] | 10.34 | 359,915 [assumed] | |
| | | RF Power Applied | 0.000028729 | 0.001388 [assumed] | 2.96 (5.7% greater than actual value of 2.8 lbs) | 103,039 | 0.2863 [assumed] |
| | | Case C- Calculations Based on RF/R.T. Ratio fo 0.006" O.D. SS304 Cable Tested and Tensile Strength of 349 KSI fo 6 Mil Cable | | | | | |
| SS304 | 0.00694 | Room Temperature | 0.000028729 | 0.001388 [assumed] | 10.03 | 349,193 [assumed] | |
| | | RF Power Applied | 0.000028729 | 0.001388 [assumed] | 1.37 | 47,765 [assumed] | 0.1368 |

What is claimed is:

1. Apparatus for electrosurgically cutting about a tissue volume, comprising:

a support member having an outer surface surmounting an interior channel and extending along an instrument axis to a forward region;

a tissue capture component positioned within said interior channel, having a leaf assembly comprising a plurality of elongate thin leafs extending forwardly from a base portion, a said leaf having a thickness extending between oppositely disposed faces, having a leaf width extending between oppositely disposed side edges and extending a leaf length along a centrally disposed leaf axis to a tip region having a forward edge, having a cable guide channel extending along said leaf to a guide outlet at said tip region, and having an eyelet structure extending forwardly from the location of said forward edge with an eyelet width extending substantially continuously along said leaf length effective to withstand tissue cutting loads, having a surface substantially perpendicular to a said leaf face and having a cable receiving aperture extending therethrough said leaf assembly being moveable to deploy outwardly from said support member forward region, said capture component having a pursing cable assembly extending through said cable guide channel, said guide outlet, and said cable receiving aperture of each said leaf, electrosurgically energizable and deployable with each said leaf tip region to define an electrosurgical cutting arc of initially expanding extent and subsequent contracting extent;

a drive assembly engageable with said leaf assembly base portion and said pursing cable assembly and actuable to move said leaf assembly to deploy outwardly from said support member while effecting said deployment of said pursing cable assembly; and a control assembly drivably engageable with said drive assembly to effect said actuation thereof and having a terminal electrically coupled with said cable assembly to effect the electrosurgical energization thereof.

2. The apparatus of claim 1 in which:

said leaf eyelet structure is formed integrally with said tip region and is twisted thereupon to define said surface substantially perpendicular to said leaf face.

3. The apparatus of claim 2 in which said defined surface substantially perpendicular to said leaf face is substantially parallel with said leaf axis.

4. The apparatus of claim 2 in which:

said leaf eyelet structure is configured having oppositely disposed eyelet edges spaced apart to define said substantially constant eyelet width, an aligned said eyelet edge being configured prior to said twisting as an extension of a coextensive said leaf side edge.

5. The apparatus of claim 4 in which:

said eyelet edge opposite said aligned eyelet edge is substantially parallel with a said leaf face.

6. The apparatus of claim 4 in which:

said leaf tip region forward edge is slanted inwardly toward said base portion from a location of adjacency with said eyelet edge opposite said aligned eyelet edge; and said leaf eyelet structure is twisted in combination with a portion of said tip region to define said surface substantially perpendicular to said leaf face.

7. The apparatus of claim 1 in which:

said leaf eyelet structure is configured having oppositely disposed eyelet edges spaced apart to define said substantially constant eyelet width, an aligned said eyelet edge being configured as an extension of a coextensive said leaf side edge.

8. The apparatus of claim 7 in which:

said leaf eyelet structure is formed integrally with said tip region, and is bent outwardly to define said surface substantially perpendicular to said leaf face along a bend line extending inwardly toward said base portion at an acute angle with respect to said leaf axis to said coextensive leaf edge.

9. The apparatus of claim 8 in which:

said acute angle is in a range of from about 22° to about 28°.

10. The apparatus of claim 8 in which:

said bend line extends from said tip region forward edge at a location adjacent said leaf eyelet structure eyelet edge opposite said aligned opposite edge to said coextensive leaf edge.

11. The apparatus of claim 10 in which;

said acute angle is about 28°.

12. The apparatus of claim 11 in which:

said eyelet edges are substantially parallel; and said eyelet edges extend outwardly from a said leaf face at an angle of about 28°.

13. The apparatus of claim 8 in which:

said cable guide channel extends along said leaf to locate said guide outlet substantially at said leaf axis centrally between said oppositely disposed leaf side edges; and said acute angle locates said eyelet structure cable receiving aperture forwardly of said guide outlet and in adjacency with said leaf axis.

14. The apparatus of claim 8 in which:

said bend line extends from a position on a said eyelet edge opposite said aligned eyelet edge and located inwardly from said cable receiving aperture to said coextensive leaf edge.

15. The apparatus of claim 14 in which:

said acute angle is about 22°.

16. The apparatus of claim 14 in which:

said eyelet edges are substantially parallel; and said eyelet edges extend outwardly from a said leaf face at an angle of about 22°.

17. The apparatus of claim 1 in which:

said leaf eyelet structure is formed integrally with said tip region; and said leaf eyelet structure is configured having oppositely disposed eyelet edges spaced apart to define said eyelet width, an interior said eyelet edge extending from said tip region forward edge at an acute angle with respect to and diagonally toward said leaf axis, said leaf eyelet structure being bent outwardly to define said surface substantially perpendicular to said leaf face along a bend line aligned with said interior eyelet edge and extending within said tip region to a said leaf side edge.

18. The apparatus of claim 17 in which:

said acute angle is about 35°.

19. The apparatus of claim 17 in which:

said cable guide channel extends along said leaf to locate said guide outlet substantially at said leaf axis; and said acute angle locates said eyelet structure cable receiving aperture forwardly of said guide outlet and about said leaf axis.

20. The apparatus of claim 17 in which:

said oppositely disposed eyelet edges are spaced apart to define a substantially constant said eyelet width.

21. The apparatus of claim 19 in which:

said leaf tip region forward edge is slanted inwardly toward said base portion from a location of adjacency with said interior eyelet edge.

22. The apparatus of claim 1 in which:

said leaf eyelet structure is formed integrally with said tip region; and said leaf eyelet structure is configured having oppositely disposed eyelet edges spaced apart to define said eyelet width, an interiorly disposed aligned said eyelet edge being configured as an extension of a coextensive said leaf side edge, said leaf eyelet structure being bent outwardly to define said surface substantially perpendicular to said leaf face along a bend line aligned with said interiorly disposed aligned said eyelet edge.

23. The apparatus of claim 22 in which:

said interiorly disposed aligned said eyelet edge is substantially coplanar with a said leaf face.

24. The apparatus of claim 22 in which:

said leaf tip region forward edge is slanted inwardly toward said base portion from a location of adjacency with said interiorly disposed aligned eyelet edge.

25. The apparatus of claim 1 in which:

said pursing cable assembly is configured with a multiple-strand, electrically conductive cable having a tensile strength of at least about 90,000 p.s.i. at the temperature of an electrosurgical cutting arc.

26. The apparatus of claim 1 in which:

said pursing cable assembly is configured with a multi-strand type 316 stainless steel cable.

27. The apparatus of claim 26 in which:

said multi-strand stainless steel cable has a diameter of about 0.005 inch to about 0.008 inch.

28. The apparatus of claim 1 in which:

said pursing cable assembly is configured as a multi-strand cable formed of a material selected from the group comprising: type 316 stainless steel, nickel-based alloys, martensitic stainless steels, and tungsten and tungsten-based alloys.

29. The apparatus of claim 28 in which:

said multi-strand stainless steel cable has a diameter of about 0.005 inch to about 0.008 inch.

30. Apparatus for electrosurgically cutting about a tissue volume, comprising:

a support member having an outer surface surmounting an interior channel and extending along an instrument axis to a forward region;

a capture component positioned within said support member forward region, having a forward portion extending to a forwardly disposed pursing cable assembly configured with at least one electrically conductive multi-strand cable energizable to provide an electrosurgical cutting arc leading edge portion, said cable exhibiting a strength supporting a load in tension greater than about one pound, in the temperature environment of said cutting arc, said cable extending into said interior channel, said leading edge of said forward portion being extendible from said support member forward region toward an outer peripheral orientation having a diametric extent and subsequently being drawn in contraction toward said instrument axis by stress asserted upon said cable assembly reaching a load value of about one pound upon a cable;

a drive assembly extending from drive engagement with said capture component to a driven engagement portion drivably moveable to effect extension of said leading edge and to apply said stress to said cable assembly; and an actuator and control assembly drivably engageable with said drive assembly driven engagement portion to effect said movement thereof and to convey electrosurgical cutting energy to said cable assembly.

31. The apparatus of claim 30 in which:

said multi-strand cable exhibits an overall diameter within a range from about 6 mils to about 7 mils.

32. The apparatus of claim 30 in which:

said multi-strand cable is formed of a type 316 stainless steel.

33. The apparatus of claim 32 in which:

said cable comprises 19 strands each having a diameter of about 1.0 mils to about 1.6 mils.

34. The apparatus of claim 33 in which:

each said strand is formed of stainless steel with the formulation; 0.08% maximum carbon, 2.00% maximum manganese, 0.045% maximum potassium, 0.030% maximum sulfur, 1.00% maximum silicon, 16.00% to 18.00% chromium, 10.00% to 14% nickel, and 2.00% to 3.00% molybdenum.

35. The apparatus of claim 34 in which:

each said strand is formed with stainless steel with the formulation: 0.03% maximum carbon, 2.00% maximum manganese, 0.045% maximum potassium, 0.030% maximum sulfur, 1.00% maximum silicon, 16.00% to 18.00% chromium, 10.00% to 14% nickel, and 2.00% to 3.00% molybdenum.

36. The apparatus of claim 33 in which:

each said strand is formed of a nickel-based alloy with the formulation: 0.08 to 0.12 weight percent carbon, 1.0, weight percent manganese, 1.0 weight percent silicon, 4.0 to 7.0 weight present tungsten, 3.0 to 5.25 weight percent molybdenum, 15 to 18 weight percent chromium, 2.5 weight percent cobalt, 0.2 to 0.4 weight percent vanadium, 0.04 weight percent phosphorous, 0.03 weight percent sulfur, balance, nickel.

37. The apparatus of claim 33 in which:

each said strand is formed of a nickel-based alloy, with the formulation: 18.0 to 20.0 weight percent chromium, 10.0 to 12.0 (max) weight percent cobalt, 9.0 to 10.5 weight percent carbon, 0.5 weight percent silicon, 0.1 weight percent manganese, 3.0 to 3.3 weight percent titanium, 1.4 to 1.6 weight percent aluminum, balance, nickel.

38. The apparatus of claim 33 in which:

each said strand is formed of a nickel-based alloy with the formulation: 0.08 weight percent carbon, 0.35 weight percent manganese 50 to 55 weight percent nickel, 17 to 21 weight percent chromium, 4.75 to 5.5 weight percent cobalt and tantalum, 2.8 to 3.3 weight percent molybdenum, 1.0 weight percent cobalt, 0.65 to 1.5 weight percent titanium, 0.2 to 0.8 weight percent aluminum, 0.35 weight percent silicon, 0.3 weight percent copper, 0.015 weight percent phosphorous, 0.006 weight percent boron, balance, iron.

39. The apparatus of claim 33 in which:

each said strand is formed of martensitic stainless steel with the formulation: 0.15 (max) weight percent carbon, 11.5 to 13.5 weight percent chromium, 1.25 to 2.5 weight percent nickel, 1.00 (max) weight percent manganese, 1.0 (max) weight percent silicon, 0.040 (max) weight percent phosphorous, 0.030 (max) sulfur.

40. The apparatus of claim 33 in which:

each said strand is formed of martensitic stainless steel with the formulation: 0.20 (max) weight percent carbon, 15 to 17 weight percent chromium, 1.25 to 2.50 weight percent nickel, 1.00 (max) weight percent manganese, 0.040 (max) weight percent phosphorous, 0.030 (max) weight percent sulfur, 1.00 (max) weight percent silicon, balance, iron.

41. The apparatus of claim 33 in which:

each said strand is formed of tungsten alloyed with about 26 weight percent aluminum.

42. Apparatus for electrosurgically cutting about a tissue volume, comprising:

a support member extending to a forward region positionable in adjacency with said tissue volume;

a cutting component at said forward region having a multi-strand cable formed of a type 316 stainless steel with a lead portion of said cable being responsive to applied electrosurgical cutting energy to support an electrosurgical cutting arc while moving in cutting relationship along a cutting locus through tissue, said cable exhibiting a tensile load at a region of said locus; and an actuator assembly coupled with said cable and applying said electrosurgical energy and tensile load thereto.

43. The apparatus of claim 42 in which:

said multi-strand cable exhibits a diameter within a range from about 6 mils to about 8 mils.

44. The apparatus of claim 42 in which:

said cable comprises 19 strands each having a diameter of about 1.4 mils.

45. The apparatus of claim 43 in which:

said multi-strand cable is configured to support a said load which is greater than one pound at a temperature of the environment of said electrosurgical cutting arc.

* * * * *